(12) United States Patent
Holtcamp et al.

(10) Patent No.: US 8,524,930 B2
(45) Date of Patent: Sep. 3, 2013

(54) CLASS OF OLEFIN METATHESIS CATALYSTS, METHODS OF PREPARATION, AND PROCESSES FOR THE USE THEREOF

(75) Inventors: Matthew W. Holtcamp, Humble, TX (US); Matthew S. Bedoya, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 288 days.

(21) Appl. No.: 13/149,012

(22) Filed: May 31, 2011

(65) Prior Publication Data

US 2012/0309998 A1    Dec. 6, 2012

(51) Int. Cl.
*C07F 15/00*    (2006.01)
*C07C 2/04*    (2006.01)
*C08F 4/80*    (2006.01)

(52) U.S. Cl.
USPC ............. 556/20; 526/171; 585/360; 585/507; 585/508; 585/509

(58) Field of Classification Search
USPC .................. 556/20; 585/360, 507, 508, 509; 526/171
See application file for complete search history.

(56) References Cited

U.S. PATENT DOCUMENTS

| 5,312,940 | A | 5/1994 | Grubbs et al. |
| 5,342,909 | A | 8/1994 | Grubbs et al. |
| 5,710,298 | A | 1/1998 | Grubbs et al. |
| 5,728,917 | A | 3/1998 | Grubbs et al. |
| 5,750,815 | A | 5/1998 | Grubbs et al. |
| 5,831,108 | A | 11/1998 | Grubbs et al. |
| 6,306,988 | B1 | 10/2001 | Grubbs et al. |
| 6,323,296 | B1 | 11/2001 | Warner et al. |
| 6,803,429 | B2 | 10/2004 | Morgan et al. |

(Continued)

FOREIGN PATENT DOCUMENTS

| EP | 0 424 833 A2 * | 5/1991 |
| WO | WO 97/20865 | 6/1997 |

(Continued)

OTHER PUBLICATIONS

Jacobsen, "P-Heterocyclic Carbenes as Potential Ligands in the Design of New Metathesis Catalysts. A Computational Study", The Royal Society of Chemistry, Dalton Translations, 2006, vol. 18, pp. 2214-2224.

(Continued)

*Primary Examiner* — Porfirio Nazario Gonzalez
(74) *Attorney, Agent, or Firm* — Catherine L. Bell

(57) ABSTRACT

This invention relates to a metathesis catalyst comprising a Group 8 metal complex represented by the formula:

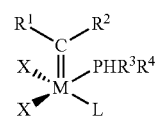

wherein:
M is a Group 8 metal; each X is independently an anionic ligand; $R^1$ and $R^2$ are independently selected from the group consisting of hydrogen, a $C_1$ to $C_{30}$ hydrocarbyl, and a $C_1$ to $C_{30}$ substituted hydrocarbyl; $R^3$ and $R^4$ are independently selected from the group consisting of hydrogen, $C_1$ to $C_{12}$ hydrocarbyl groups, substituted $C_1$ to $C_{12}$ hydrocarbyl groups, and halides; and L is a neutral donor ligand. This invention also relates to processes for performing a metathesis reaction, in particular ring opening cross metathesis reactions and ring opening metathesis polymerization reactions, using the Group 8 metal complexes.

46 Claims, 2 Drawing Sheets

Molecular Structure of [(HP(tBu)$_2$)$_2$Ru(C$_5$H$_8$)Cl$_2$]

(56) References Cited

U.S. PATENT DOCUMENTS

| | | | |
|---|---|---|---|
| 7,294,717 | B2 | 11/2007 | Herrmann et al. |
| 7,329,758 | B1 | 2/2008 | Grubbs et al. |
| 2002/0015519 | A1 | 2/2002 | Tokas et al. |
| 2004/0225073 | A1 | 11/2004 | Angeletakis et al. |

FOREIGN PATENT DOCUMENTS

| WO | WO 97/29135 | 8/1997 |
|---|---|---|
| WO | 02-26857 | 4/2002 |
| WO | WO 2008/010961 | 1/2008 |

OTHER PUBLICATIONS

Mathew et al., "*Assessment of Stereoelectronic Effects in Grubbs First-Generation Olefin Metathesis Catalysis Using Molecular Electrostatic Potential*", Organometallics, 2011, vol. 30, No. 6, pp. 1438-1444.

Pereira da Silva et al., "*Investigation of the Catalysis Mechanism of ROMP of Norbornene Using Density Functional Theory*", Quimica Nova, 2010, vol. 33, No. 7, pp. 1444-1448 (Abstract only).

Randall et al., "*Selective Ring-Opening Cross-Metathesis. Short Syntheses of Multifidene and Viridiene*", Journal of American Chemical Society, 1995, vol. 117, No. 37, pp. 9610-9611.

Sliwa et al., "*Assessment of Density Functional Methods for the Study of Olefin Metathesis Catalysed by Ruthenium Alkylidene Complexes*", Chemical Physics Letters, 2010, vol. 493, Nos. 4-6, pp. 273-278.

Burdett et al., "*Renewable Monomer Feedstocks via Olefin Metathesis: Fundamental Mechanistic Studies of Methyl Oleate Ethenolysis with the First-Generation Grubbs Catalyst*", Organometallics 2004, vol. 23, No. 9, pp. 2027-2047.

Kingsbury et al., "*A Recyclable Ru-Based Metathesis Catalyst*", J. Am. Chem. Soc. 1999, vol. 121, No. 4, pp. 791-799.

Tupy et al., Final Technical Report entitled "*Platform Chemicals from an Oilseed Biorefinery*", Grant No. DE-FG36-04GO14016, awarded by the Department of Energy, (2006).

Wilhelm et al., "*Reactivity of $Ru(H)(H_2)Cl(PCy_3)_2$ with Propargyl and Vinyl Chlorides: New Methodology To Give Metathesis-Active Ruthenium Carbenes*", Organometallics, 1997, No. 16, No. 18, pp. 3867-3869.

\* cited by examiner

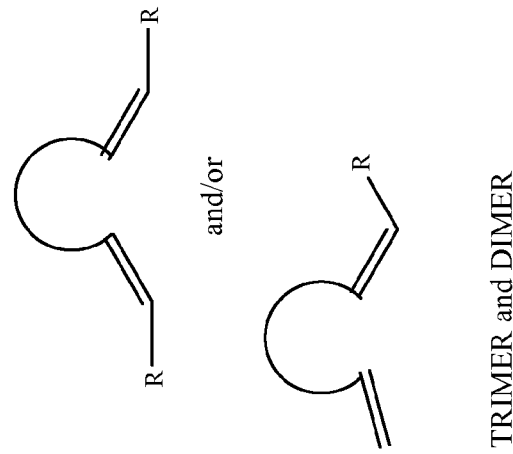
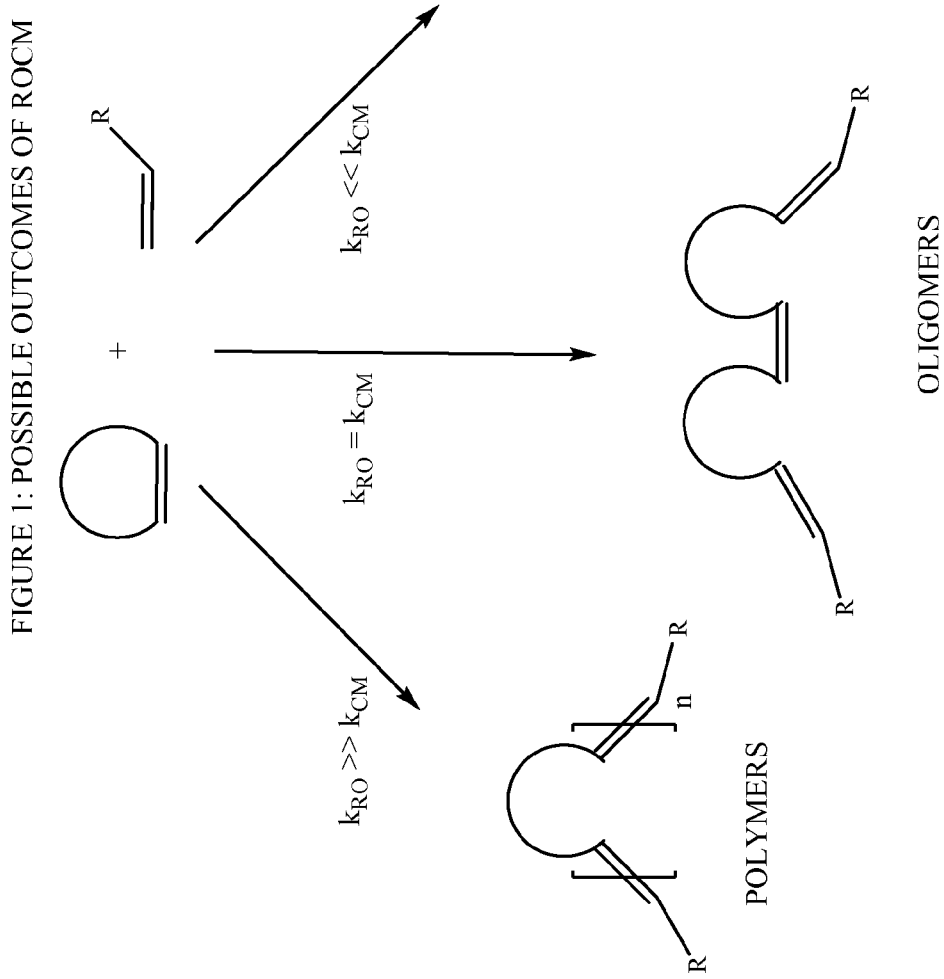

FIGURE 2: Molecular Structure of [(HP(tBu)$_2$)$_2$Ru(C$_5$H$_8$)Cl$_2$]
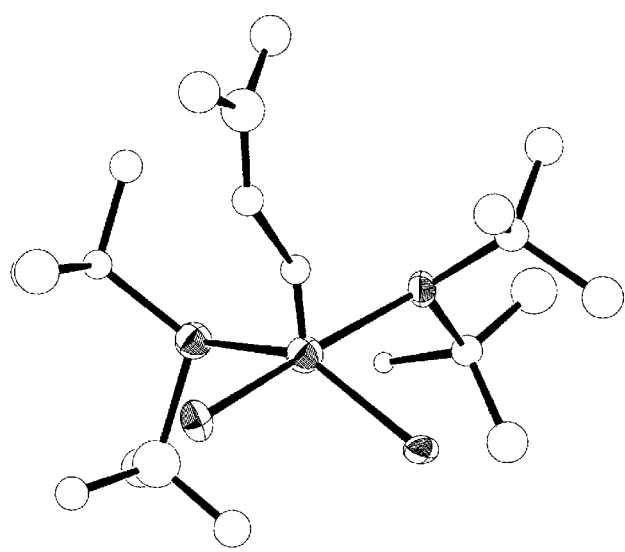

CLASS OF OLEFIN METATHESIS CATALYSTS, METHODS OF PREPARATION, AND PROCESSES FOR THE USE THEREOF

STATEMENT OF RELATED CASES

This application relates to U.S. Ser. No. 12/143,663, filed on Jun. 20, 2008; U.S. Ser. No. 12/487,739, filed on Jun. 19, 2009; U.S. Ser. No. 12/488,066, filed on June. 19, 2009; U.S. Ser. No. 12/488,093, filed on Jun. 19, 2009; U.S. Ser. No. 61/259,514, filed on Nov. 9, 2009; U.S. Ser. No. 12/939,054, filed on Nov. 3, 2010; U.S. Ser. No. 61/259,521, filed on Nov. 9, 2009; U.S. Ser. No. 12/939,063, filed on Nov. 3, 2010; U.S. Ser. No. 12/705,136, filed on Feb. 12, 2010; U.S. Ser. No. 61/314,388, filed on Mar. 16, 2010; U.S. Ser. No. 12/939,024, filed Nov. 3, 2010; U.S. Ser. No. 61/203,523, filed on Dec. 23, 2008; U.S. Ser. No. 12/653,742, filed Dec. 7, 2009; U.S. Ser. No. 61/210,045, filed Mar. 13, 2009; U.S. Ser. No. 12/660, 815, filed on Mar. 4, 2010; U.S. Ser. No. 61/025,076, filed on Jan. 31, 2008; U.S. Ser. No. 61/025,200, filed Jan. 31, 2008; U.S. Ser. No. 12/341,830, filed Dec. 22, 2008; U.S. Ser. No. 61/376,925 filed on Aug. 25, 2010; and U.S. Ser. No. 12/890, 315 filed Sep. 24, 2010.

FIELD OF THE INVENTION

This invention relates to a novel class of olefin metathesis catalysts, methods of preparation, and to processes using the olefin metathesis catalysts.

BACKGROUND OF THE INVENTION

In organic synthesis, a metathesis reaction is a catalytic reaction in which recombination of the double bonds occurs between two kinds of olefins or acetylenes (also referred to as alkynes). The diversity of possible applications has led to the use of metathesis, particularly olefin metathesis, as a standard synthetic tool. Olefin metathesis applications include cross-metathesis (CM), ring-opening metathesis polymerization (ROMP), ring-opening cross metathesis (ROCM), ring-closing metathesis (RCM), and acyclic diene metathesis (AD-MET). CM involves a carbon-carbon bond breaking/bond making process in which there is an overall exchange of double bond moieties between two olefins. ROMP involves the formation of polyolefins from the ring opening of cyclic olefins; ROCM involves a tandem sequence in which a cyclic olefin is opened and a second acyclic olefin is then cross metathesized onto the newly formed olefin termini; RCM involves the intramolecular transformation of an alpha, omega-diene to a cyclic olefin; and ADMET involves the polymerization of terminal dienes to polyenes. These synthetic tools have been applied to solve a wide range of synthetic problems, for example, RCM has been often featured as a key step in many synthetic solutions ranging from the total synthesis of natural products to the synthesis of catenanes. Also, industrially important polymers produced from ROMP include trans-polyoctenamer (polymer of cyclooctene, commercially available as Vestenamer® from Evonik Industries), polynorbornene (commercially available as Norsorex®); and polydicyclopentadiene (commercially available as Telene®, Metton®, and Pentam®). Another commercially significant application is ethenolysis, which is the CM of ethylene and internal olefins to produce alpha-olefins. Metathesis reactions are therefore indispensable as a synthetic tool for the formation of new carbon-carbon bonds.

Olefin metathesis may be catalyzed by one or more catalytic metals, usually one or more transition metals, such as the molybdenum-containing Schrock catalyst and the ruthenium- or osmium-containing Grubbs catalysts. Single component ruthenium or osmium catalysts have been previously described by, for example, U.S. Pat. Nos. 5,312,940; 5,342, 909; 5,728,917; 5,710,298; 5,750,815; 5,831,108; 7,329,758; and PCT Publications WO 97/20865 and WO 97/29135, which are all incorporated herein by reference. These catalysts possess several advantageous properties, such as tolerance to a variety of functional groups and higher activity than previously known metathesis catalysts.

The ethenolysis of an internal olefin to produce linear alpha-olefins (LAOS) is of particular commercial significance. LAOs are useful as monomers or comonomers to produce polyalphaolefins (PAOs) and/or as intermediates in the production of epoxides, amines, oxo alcohols, synthetic lubricants, synthetic fatty acids, and alkylated aromatics. LAOs of industrial importance include 1-butene, 1-hexene, 1-octene, 1-decene, 1-undecene, 1-dodecene, and 1-tetradecene. However, the production of LAOs is often undesirably inefficient, creates unwanted by-products, and wastes reactants and energy. Also, the major source of the starting materials for these commercial routes to LAOs is nonrenewable feedstreams including petroleum, coal, and natural gas.

Recently there has been a strong incentive to produce fuels and chemical products from renewable feedstreams such as natural oils. For example, the development of biodiesel fuels is of great interest and some biodiesel-based materials are already commercially produced. Specifically, demand for bio-diesel fuels made from plant oils is expected to increase significantly over the next decade. LAOs may be produced from such renewable feedstreams by a CM reaction of the renewable feedstream, such as methyl oleate, with an olefin, such as ethylene, in the presence of a metathesis catalyst.

CM catalysts reported thus far for the ethenolysis of methyl oleate are typically ruthenium-based catalysts bearing phosphine or carbene ligands, such as those reported in Organometallics 2004, 23, 2027 and WO 2008/010961. However, these catalysts were reported to be too expensive for industrial consideration due to high costs associated with the catalysts being derived from a low yielding synthesis (See Final Technical Report entitled "Platform Chemicals from an Oilseed Biorefinery," grant number DE-FG36-04GO14016, awarded by the Department of Energy). Furthermore, these ruthenium alkylidene catalysts are usually prepared by the reaction of ruthenium species with diazo compounds (J. Am. Chem. Soc. 1999, 121, 791). Therefore, cost and safety concerns associated with industrial scale reactions comprising diazo compounds have led to increased efforts to prepare ruthenium alkylidenes via alternate synthetic routes, such as using propargyl and vinyl chlorides (Organometallics, 1997, 16, 3867). In order to obtain a commercially viable metathesis-based process, for example, LAO production via the CM of ethylene and biodiesel or natural oils, higher activity metathesis catalysts must be discovered.

There remains a need for catalysts which demonstrate high activity and selectivity in metathesis transformations which are capable of being synthesized by mild, affordable, and simple synthetic routes. The new catalysts disclosed herein are useful for metathesis transformations, particularly ROCM and ROMP. The inventors have surprisingly found that a metathesis catalyst comprising a Group 8 metal complex is an active metathesis catalyst, particularly for ROCM and ROMP transformations. The metathesis catalysts of the present invention provide mild, affordable, and simple synthetic routes to desirable olefins and polyolefins, poly(cyclic olefins), and other industrially relevant chemicals.

SUMMARY OF THE INVENTION

The invention relates to metathesis catalysts comprising a Group 8 metal complex represented by the formula:

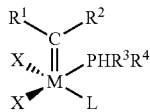

wherein:
M is a Group 8 metal;
each X is independently an anionic ligand;
$R^1$ and $R^2$ are independently selected from the group consisting of hydrogen, a $C_1$ to $C_{30}$ hydrocarbyl, and a $C_1$ to $C_{30}$ substituted hydrocarbyl;
$R^3$ and $R^4$ are independently selected from the group consisting of hydrogen, $C_1$ to $C_{12}$ hydrocarbyl groups, substituted $C_1$ to $C_{12}$ hydrocarbyl groups, and halides; and
L is a neutral donor ligand.

The invention also relates to processes for performing a metathesis reaction comprising:
(i) contacting one or more olefins with a metathesis catalyst; wherein the metathesis catalyst comprises a Group 8 metal complex represented by the formula:

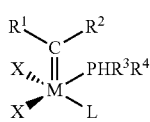

wherein:
M is a Group 8 metal;
each X is independently an anionic ligand;
$R^1$ and $R^2$ are independently selected from the group consisting of hydrogen, a $C_1$ to $C_{30}$ hydrocarbyl, and a $C_1$ to $C_{30}$ substituted hydrocarbyl;
$R^3$ and $R^4$ are independently selected from the group consisting of hydrogen, $C_1$ to $C_{12}$ hydrocarbyl groups, substituted $C_1$ to $C_{12}$ hydrocarbyl groups, and halides;
L is a neutral donor ligand; and
(ii) obtaining at least one metathesis product.

BRIEF DESCRIPTION OF THE FIGURES

FIG. 1 is a representation of some of the possible outcomes of ring opening cross metathesis.

FIG. 2 is the molecular structure of [(HP(tert-butyl)$_2$)$_2$Ru($C_5H_8$)Cl$_2$], with hydrogen atoms omitted for clarity.

DETAILED DESCRIPTION

In recent years, the use of Group 8 metal complexes as catalysts in olefin polymerization processes (RCM, ROMP, ROCM) and olefin metathesis processes (CM, ADMET) has increased, mainly due to their remarkable stability towards diverse functional groups and protic solvents, and their ease of handling. However, catalysts which demonstrate high activity and selectivity in metathesis transformations are still desired.

The present invention comprises novel catalysts useful for the metathesis of olefins and processes for the use thereof. In particular, the inventive catalysts demonstrate unexpected selectivity for the ROCM dimer product in ROCM transformations.

Definitions

For the purposes of this invention and the claims thereto, the new numbering scheme for the Periodic Table Groups is used as in CHEMICAL AND ENGINEERING NEWS, 63(5), 27 (1985). For the purposes of this invention and claims thereto, a "Group 8 metal" is an element from Group 8 of the Periodic Table.

For the purposes of this invention and the claims thereto, a "substituted hydrocarbyl" is a radical made of carbon and hydrogen where at least one hydrogen is replaced by a heteroatom, preferably one or more of N, O, S, and P.

For purposes of this invention and claims thereto, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may comprise at least one aromatic group. Preferred alkoxides include a $C_1$ to $C_{10}$ alkyl group, preferably methyl, ethyl, propyl, butyl, or isopropyl. Preferred alkoxides include those where the alkyl group is a phenol, substituted phenol (where the phenol may be substituted with up to 1, 2, 3, 4, or 5 $C_1$ to $C_{12}$ hydrocarbyl groups) or a $C_1$ to $C_{10}$ hydrocarbyl, preferably a $C_1$ to $C_{10}$ alkyl group, preferably methyl, ethyl, propyl, butyl, or phenyl.

For the purposes of this invention and the claims thereto, when a polymer, copolymer, oligomer, or co-oligomer is referred to as "comprising an olefin," including, but not limited to decene and/or ethylene, the olefin present in such polymer, copolymer, oligomer, or co-oligomer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. The term "different" as used to refer to mer units indicates that the mer units differ from each other by at least one atom or are different isomerically. An "oligomer" is a polymer having 2 to 100 mer units, where the mer units may be the same or different. Exemplary oligomers include dimers (two mer units), trimers (three mer units), tetramers (four mer units), decamers (ten mer units), and so on.

An "olefin," alternatively referred to as "alkene," is a linear, branched, or cyclic compound of carbon and hydrogen having at least one double bond. An "alpha-olefin" is an olefin having a double bond at the alpha (or 1–) position. A "linear alpha-olefin" or "LAO" is C4+ olefin (typically C4 to C50) with a double bond at the alpha position and a linear hydrocarbon chain. A "polyalphaolefin" or "PAO" is a polymer having at least two mer units.

An "anionic ligand" is a negatively charged ligand which donates one or more pairs of electrons to a metal ion. A "neutral donor ligand" is a neutrally charged ligand which donates one or more pairs of electrons to a metal ion.

For the purposes of this invention and the claims thereto, when catalysts are described as comprising neutral stable forms of the components, it is well understood by one of ordinary skill in the art, that the ionic form of the component is the form that reacts with the monomers to produce polymers. In the description herein, the transition metal compound used for catalysis may be described as a catalyst precursor, a pre-catalyst compound, a catalyst, or a catalyst compound, and these terms are used interchangeably.

Additionally, a "reactor" is any container(s) in which a chemical reaction occurs.

Metathesis Catalysts

This invention relates to a metathesis catalyst comprising: a Group 8 metal complex represented by the formula:

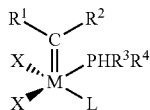

wherein:

M is a Group 8 metal (preferably M is ruthenium or osmium, preferably ruthenium);

each X is independently an anionic ligand (preferably selected from the group consisting of halides, alkoxides, aryloxides, and alkyl sulfonates, preferably a halide, preferably chloride);

$R^1$ and $R^2$ are independently selected from the group consisting of hydrogen, a $C_1$ to $C_{30}$ hydrocarbyl, and a $C_1$ to $C_{30}$ substituted hydrocarbyl (preferably $R^1$ and $R^2$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl);

$R^3$ and $R^4$ are independently selected from the group consisting of hydrogen, $C_1$ to $C_{12}$ hydrocarbyl groups, substituted $C_1$ to $C_{12}$ hydrocarbyl groups, and halides (preferably $R^3$ and $R^4$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl); and L is a neutral donor ligand, preferably L is selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; preferably a phosphine, a sulfonated phosphine, an N-heterocyclic carbene, a cyclic alkyl amino carbene, and substituted analogs thereof (preferably L is selected from a phosphine, an N-heterocyclic carbene, a cyclic alkyl amino carbene, and substituted analogs thereof).

For purposes of this invention and claims thereto, a "cyclic carbene" may be defined as a cyclic compound with a neutral dicoordinate carbon center featuring a lone pair of electrons. Such cyclic carbenes may be represented by the formula (II) below:

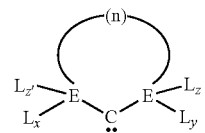

where:

n is a linking group comprising from one to four ring vertices selected from the group consisting of C, Si, N, P, O, and S, with available valences optionally occupied by H, oxo, hydrocarbyl, or substituted hydrocarbyl groups; preferably, n comprises two ring vertices of carbon with available valences occupied by H, oxo, hydrocarbyl or substituted hydrocarbyl groups; preferably n is $C_2H_2$, $C_2H_4$, or substituted versions thereof;

each E is independently selected from the group comprising C, N, S, O, and P, with available valences optionally occupied by Lx, Ly, Lz, and Lz'; preferably, at least one E is a C; preferably, one E is a C and the other E is a N; preferably, both E's are C; and Lx, Ly, Lz, and Lz' are independently selected from the group comprising hydrogen, hydrocarbyl groups, and substituted hydrocarbyl groups; preferably, Lx, Ly, Lz, and Lz' are independently selected from the group comprising a hydrocarbyl group and substituted hydrocarbyl group having 1 to 40 carbon atoms; preferably, Lx, Ly, Lz, and Lz' are independently selected from the group comprising $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl, and substituted aryl; preferably, Lx, Ly, Lz, and Lz' are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, tolulyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Examples of cyclic carbenes useful in embodiments of the present invention include:

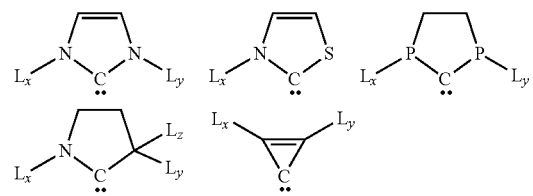

where Lx, Ly, and Lz are as defined above. In some embodiments, at least two of Lx, Ly, Lz, and Lz' may be joined to form a 3- to 12-membered spirocyclic ring, with available valences optionally occupied by H, oxo, halogens, hydrocarbyl or substituted hydrocarbyl groups. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Preferred cyclic carbenes include N-heterocyclic carbenes (NHCs). For purposes of this invention and claims thereto, NHCs are cyclic carbenes of the types described in Formula II above, where each E is N and the available valences on the N are occupied by Lx and Ly.

Preferred NHCs may be represented by the formula:

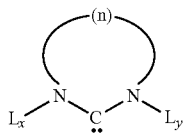

where:

n, Lx, and Ly are as described above.

Some particularly useful NHCs include:

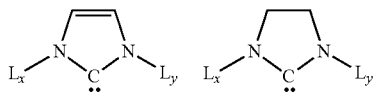

where Lx and Ly are as described above. Other useful NHCs include the compounds described in Hermann, W. A. Chem. Eur. J. 1996, 2, 772 and 1627; Enders, D. et al., Angew. Chem. Int. Ed. 1995, 34, 1021; Alder R. W., Angew. Chem. Int. Ed. 1996, 35, 1121; U.S. Ser. No. 61/314,388; and Bertrand, G. et al., Chem. Rev. 2000, 100, 39.

Particularly preferred cyclic carbenes include cyclic alkyl amino carbines (CAACs). In all embodiments herein, CAACs are cyclic carbenes of the types described in Formula II above, where one E is N and the other E is C, and the available valences on the N and C are occupied by Lx, Ly, and Lz. CAACs may be represented by the formula:

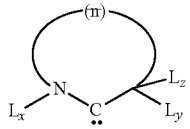

where:

n, Lx, Ly, and Lz are as described above.

Some particularly useful CAACs include:

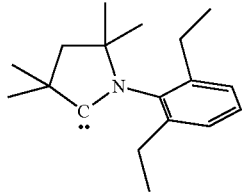

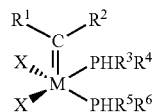

Other useful CAACs include the compounds described in U.S. Pat. No. 7,312,331; U.S. Ser. No. 61/259,514; and Bertrand et al, Angew. Chem. Int. Ed. 2005, 44, 7236-7239.

Other carbenes useful in embodiments of the present invention include thiazolyidenes, P-heterocyclic carbenes (PHCs), and cyclopropenylidenes.

With respect to Group 8 metal complexes, the phosphine ligands ($PHR^3R^4$) and L are neutral donor ligands. In some embodiments, L may also be a phosphine having a formula $PHR^5R^6$. In such embodiments, the Group 8 metal complex may be represented by the formula:

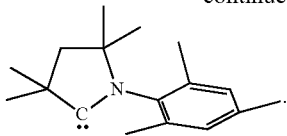

wherein:

M is a Group 8 metal (preferably M is ruthenium or osmium, preferably ruthenium);

each X is independently an anionic ligand (preferably selected from the group consisting of halides, alkoxides, aryloxides, and alkyl sulfonates, preferably a halide, preferably chloride);

$R^1$ and $R^2$ are independently selected from the group consisting of hydrogen, a $C_1$ to $C_{30}$ hydrocarbyl, and a $C_1$ to $C_{30}$ substituted hydrocarbyl (preferably $R^1$ and $R^2$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl); and $R^3$, $R^4$, $R^5$, and $R^6$ are independently selected from the group consisting of hydrogen, $C_1$ to $C_{12}$ hydrocarbyl groups, substituted $C_1$ to $C_{12}$ hydrocarbyl groups, and halides (preferably $R^3$, $R^4$, $R^5$, and $R^6$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl).

With respect to embodiments where L is a phosphine having a formula $PHR^5R^6$, in particular embodiments, at least one phosphine ligand is a secondary phosphine ligand. In such embodiments, where at least one of the neutral donor ligands is a secondary phosphine ligand, $R^3$ and $R^4$ or $R^5$ and $R^6$ are selected from the group consisting of $C_1$ to $C_{12}$ hydrocarbyl groups, substituted $C_1$ to $C_{12}$ hydrocarbyl groups, and halides. In particular embodiments, both donor ligands are secondary phosphine ligands and $R^3$, $R^4$, $R^5$, and $R^6$ are selected from the group consisting of $C_1$ to $C_{12}$ hydrocarbyl groups, substituted $C_1$ to $C_{12}$ hydrocarbyl groups, and halides.

With respect to embodiments where L is a phosphine having a formula $PHR^5R^6$, in particular embodiments, at least one donor ligand is a primary phosphine ligand. In such embodiments where at least one of the phosphine ligands is a primary phosphine ligand, one of $R^3$ and $R^4$ or one of $R^5$ and $R^6$ is selected from the group consisting of $C_1$ to $C_{12}$ hydrocarbyl groups, substituted $C_1$ to $C_{12}$ hydrocarbyl groups, and halides. In particular embodiments, both donor ligands are primary phosphine ligands and one of $R^3$ and $R^4$ and one of $R^5$ and $R^6$ is selected from the group consisting of $C_1$ to $C_{12}$ hydrocarbyl groups, substituted $C_1$ to $C_{12}$ hydrocarbyl groups, and halides.

In some embodiments, $R^3$ and $R^4$ form a ring. With respect to embodiments where L is a phosphine having a formula $PHR^5R^6$, in particular embodiments, $R^5$ and $R^6$ form a ring. In yet other embodiments, $R^3$ and $R^4$ form a ring and $R^5$ and $R^6$ form a ring. In other embodiments, $R^3$ and at least one of $R^5$ and $R^6$ may form a ring, thereby forming a chelating phosphine ligand. In other embodiments, $R^4$ and at least one of $R^5$ and $R^6$ may form a ring, thereby forming a chelating phosphine ligand.

In particular embodiments, the Group 8 metal complex is selected from:
[(HP(tert-butyl)$_2$)$_2$Ru($C_5H_8$)$Cl_2$],
[($H_2$P(tert-butyl))$_2$Ru($C_5H_8$)$Cl_2$],
[(HP(cyclohexyl)$_2$)$_2$Ru($C_5H_8$)$Cl_2$],
[($H_2$P(cyclohexyl))$_2$Ru($C_5H_8$)$Cl_2$],
[(HP(cyclopentyl)$_2$)$_2$Ru($C_5H_8$)$Cl_2$],
[($H_2$P(cyclopentyl))$_2$Ru($C_5H_8$)$Cl_2$],
[(HP(n-butyl)$_2$)$_2$Ru($C_5H_8$)$Cl_2$],
[(H2P(n-butyl))$_2$RU($C_5H_8$)$Cl_2$],
[(HP(sec-butyl)$_2$)$_2$Ru($C_5H_8$)$Cl_2$],
[(H2P(sec-butyl))$_2$Ru($C_5H_8$)$Cl_2$], and
fluoride and bromide derivatives thereof (preferably, wherein the $Cl_2$ in the above list is replaced with $F_2$, $Br_2$, ClF, ClBr or FBr).

In certain embodiments, the catalyst employed in the process of this invention may be bound to or deposited on a solid support. In particular, the Group 8 metal complex may be bound to or deposited onto a solid support, which may simplify catalyst recovery. In addition, the support may increase catalyst strength and attrition resistance. Suitable catalyst supports include, without limitation, silicas; aluminas; silica-aluminas; aluminosilicates, including zeolites and other crystalline porous aluminosilicates; as well as titanias; zirconia; magnesium oxide; carbon; and cross-linked polymeric resins, such as functionalized cross-linked polystyrenes, e.g., chloromethyl-functionalized cross-linked polystyrenes; preferably silica or alumina. The Group 8 metal complex may be deposited onto the support by any method known to those skilled in the art, including, for example, impregnation, ion-exchange, deposition-precipitation, and vapor deposition. Alternatively, a component of the catalyst, such as the Group 8 complex, may be chemically bound to the support via one or more covalent chemical bonds, for example, the catalyst may be immobilized by one or more covalent bonds with one or more of substituents of a ligand of the Group 8 metal complex. For example, the Group 8 metal complex may be deposited onto a silica support. Further, the Group 8 metal complex may be preloaded onto the solid support before forming the catalyst of the present invention. Alternatively, the supported catalyst may be generated in situ.

If a catalyst support is used, the catalyst compound may be loaded onto the catalyst support in any amount, provided that the metathesis process of this invention proceeds to the metathesis products. Generally, the catalyst compound is loaded onto the support in an amount based on the weight of the transition metal, preferably the Group 8 metal, preferably ruthenium or osmium, relative to the total weight of the catalysts plus support. The catalyst compound may be loaded onto the support in an amount greater than about 0.01 weight percent of the Group 8 metal, based upon the weight of the catalysts plus support and preferably, greater than about 0.05 weight percent of the Group 8 metal. Generally, the catalyst compound is loaded onto the support in an amount that is less than about 20 weight percent of the Group 8 metal, and preferably less than about 10 weight percent of the Group 8 metal.

Synthesis of Metathesis Catalysts

The metathesis catalysts described herein may be synthesized by any methods known to those skilled in the art. In general, the metathesis catalysts of the present invention are made by contacting a Group 8 metal complex, such as a Group 8 alkyl halide with a non-tertiary phosphine (preferably a secondary or primary phosphine) in the presence of a base, followed by reaction with a haloacetylene, yields the inventive Group 8 metal complex.

Any of the reactants may be dissolved in a suitable solvent, include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, including those that can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable diluents/solvents also include aromatic hydrocarbons, such as toluene or xylenes, and chlorinated solvents, such as dichloromethane. In other embodiments, the reactants may be used neat, that is, in the absence of a carrier solvent.

In some embodiments, the contacting process may occur in the presence of heat, for example heat to reflux, for a time period appropriate to yield the desired metathesis catalyst. The ligand exchange reaction may occur faster in such embodiments. The contacting process may occur at a temperature of 20° C. to 300° C. (preferably 20° C. to 200° C., preferably 25° C. to 100° C., preferably 30° C. to 85° C.) for a contacting time of 0.5 seconds to 48 hours (preferably 0.25 to 24 hours, preferably 30 minutes to 2 hours).

For example, [(HP(tert-butyl)$_2$)$_2$Ru($C_5H_8$)$Cl_2$] may be synthesized by combining [RuCl$_2$(cyclooctadiene)]$_n$, $H_2$, and tBu$_2$PH in 2-butanol and in the presence of triethylamine, at 80° C. followed by reaction with 3-chloro-3-methyl-1-butyne. The crystal structure of [(HP(tert-butyl)$_2$)$_2$Ru($C_5H_8$)$Cl_2$] is represented in FIG. 2, and hydrogens have been omitted for clarity.

Metathesis Reactions

The catalysts of the present invention may be used for any metathesis reaction, in particular ROMP and ROCM, by contacting the inventive catalysts with olefins and/or acetylenes.

Embodiments herein also relate processes for performing a metathesis reaction comprising:
(i) contacting one or more olefins with a metathesis catalyst; wherein the metathesis catalyst comprises a Group 8 metal complex represented by the formula:

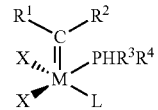

wherein:

M is a Group 8 metal (preferably M is ruthenium or osmium, preferably ruthenium);

each X is independently an anionic ligand (preferably selected from the group consisting of halides, alkoxides, aryloxides, and alkyl sulfonates, preferably a halide, preferably chloride);

$R^1$ and $R^2$ are independently selected from the group consisting of hydrogen, a $C_1$ to $C_{30}$ hydrocarbyl, and a $C_1$ to $C_{30}$ substituted hydrocarbyl (preferably $R^1$ and $R^2$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl);

$R^3$ and $R^4$ are independently selected from the group consisting of hydrogen, $C_1$ to $C_{12}$ hydrocarbyl groups, substituted $C_1$ to $C_{12}$ hydrocarbyl groups, and halides (preferably $R^3$ and $R^4$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl);

L is a neutral donor ligand, preferably L is selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; preferably a phosphine, a sulfonated phosphine, an N-heterocyclic carbene, a cyclic alkyl amino carbene, and substituted analogs thereof (preferably L is selected from a phosphine, an N-heterocyclic carbene, a cyclic alkyl amino carbene, and substituted analogs thereof); and (ii) obtaining at least one metathesis product.

Particular embodiments herein relate to processes for performing a metathesis reaction comprising:
(i) contacting one or more olefins with a metathesis catalyst; wherein the metathesis catalyst comprises a Group 8 metal complex represented by the formula:

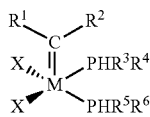

wherein:

M is a Group 8 metal (preferably M is ruthenium or osmium, preferably ruthenium);

each X is independently an anionic ligand (preferably selected from the group consisting of halides, alkoxides, aryloxides, and alkyl sulfonates, preferably a halide, preferably chloride);

$R^1$ and $R^2$ are independently selected from the group consisting of hydrogen, a $C_1$ to $C_{30}$ hydrocarbyl, and a $C_1$ to $C_{30}$ substituted hydrocarbyl;

$R^3$, $R^4$, $R^5$, and $R^6$ are independently selected from the group consisting of hydrogen, $C_1$ to $C_{12}$ hydrocarbyl groups, substituted $C_1$ to $C_{12}$ hydrocarbyl groups, and halides (preferably $R^3$, $R^4$, $R^5$, and $R^6$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl); and (ii) obtaining at least one metathesis product.

In a preferred embodiment, the reactants (for example, metathesis catalyst; olefin, optional diluent, etc.) are combined in a reaction vessel at a temperature of 20° C. to 300° C. (preferably 20° C. to 200° C., preferably 30° C. to 100° C., preferably 40° C. to 60° C.) and an olefin and/or acetylene at a pressure of 0.1 psig to 1000 psi (0.7 kPa to 6.9 MPa) (preferably 20 psi to 400 psi (0.14 MPa to 2.8 MPa), preferably 50 psi to 250 psi (0.34 MPa to 1.7 MPa)), for a residence time of 0.5 seconds to 48 hours (preferably 0.25 seconds to 5 hours, preferably 30 minutes to 2 hours).

In a preferred embodiment, the catalyst is present at from 0.001 nanomoles of transition metal per mole of cyclic olefin to 1 millimole of transition metal per mole of cyclic olefin, based upon the moles of olefin feed into the reactor. Alternately, the catalyst is present at from 0.01 nanomoles of transition metal per mole of cyclic olefin to 0.1 millimole of transition metal per mole of cyclic olefin, alternately from 0.1 nanomoles of transition metal per mole of cyclic olefin to 0.075 millimole of transition metal per mole of cyclic olefin, based upon the moles of olefin feed into the reactor.

Olefinic Reactants

Any olefin may be used in the processes for performing a metathesis reaction of this invention. The olefin may have one carbon-carbon double bond, or alternatively, two or more carbon-carbon double bonds. Since the metathesis reaction can occur at any double bond, olefins having more than one double bond will produce more metathesis products. Accordingly, in some embodiments, it is preferred to employ an olefin having only one carbon-carbon double bond. The double bond may be, without limitation, a terminal double bond or an internal double bond. The olefin may also be substituted at any position along the carbon chain with one or more substituents. In some embodiments, the one or more substituents are essentially inert with respect to the metathesis process. Suitable substituents include, without limitation, alkyl, preferably, $C_{1-6}$ alkyl; cycloalkyl, preferably, $C_{3-6}$ cycloalkyl; as well as hydroxy, ether, keto, aldehyde, and halogen functionalities. The reactant olefin may be chosen, depending on the application the metathesis product may be employed in, as illustrated in the applications below. The reactant olefin may be at least one of an acyclic olefin, an alpha olefin, a renewable feedstream, a cyclic olefin, an internal olefin, and an acetylene.

ROCM Reactions

Particular embodiments herein relate to processes wherein the metathesis reaction is a ring opening cross metathesis reaction comprising: (i) contacting a cyclic olefin and a second olefinic reactant in the presence of the Group 8 metathesis catalyst described above under conditions and for a time period sufficient to allow the ring opening cross metathesis reaction to occur; and (ii) obtaining a ring opening cross metathesis product (preferably the ring opening cross metathesis product is a dimer and is obtained in greater than 50 mol % yield, preferably in greater than 60 mol % yield, preferably in greater than 70 mol % yield, preferably in greater than 75 mol % yield, preferably in greater than 80 mol % yield).

In a preferred embodiment, the reactants (for example, metathesis catalyst; olefin, optional diluent, etc.) are combined in a reaction vessel at a temperature of 20° C. to 300° C. (preferably 20° C. to 200° C., preferably 30° C. to 100° C., preferably 40° C. to 60° C.) and an olefin and/or acetylene at a pressure of 0.1 psig to 1000 psi (0.7 kPa to 6.9 MPa)

(preferably 20 to 400 psi (0.14 MPa to 2.8 MPa), preferably 50 to 250 psi (0.34 MPa to 1.7 MPa)), for a residence time of 0.5 seconds to 48 hours (preferably 0.25 seconds to 5 hours, preferably 30 minutes to 2 hours).

In a preferred embodiment, the catalyst is present at from 0.001 nanomoles of transition metal per mole of cyclic olefin to 1 millimole of transition metal per mole of cyclic olefin, based upon the moles of olefin feed into the reactor. Alternately, the catalyst is present at from 0.01 nanomoles of transition metal per mole of cyclic olefin to 0.1 millimole of transition metal per mole of cyclic olefin, alternately from 0.1 nanomoles of transition metal per mole of cyclic olefin to 0.075 millimole of transition metal per mole of cyclic olefin, based upon the moles of olefin feed into the reactor.

Cyclic Olefins

The cyclic olefin may be a single cyclic olefin, or a combination of cyclic olefins, that is a mixture of two or more different cyclic olefins. The cyclic olefins may be strained or unstrained, monocyclic or polycyclic, and may optionally include hetero atoms and/or one or more functional groups. Suitable cyclic olefins include, but are not limited to norbornene, norbornadiene, dicyclopentadiene, cyclopentene, cycloheptene, cyclooctene, cyclooctadiene, cyclododecene, 7-oxanorbornene, 7-oxanorbornadiene, and substituted derivatives therefrom. Illustrative examples of suitable substituents include, but are not limited to, hydroxyl, thiol, ketone, aldehyde, ester, ether, amine, imine, amide, nitro, carboxylic acid, disulfide, carbonate, isocyanate, carbodiimide, carboalkoxy, and halogen. Preferred cyclic olefins include cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene, as shown below.

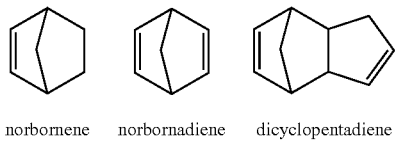

norbornene  norbornadiene  dicyclopentadiene

Second Olefinic Reactant

Any olefin may be used for the ROCM reaction with the at least one cyclic olefin. For example, a terminal olefin may be used. For the purposes of this invention and the claims thereto, the term "terminal olefin" refers to an organic compound containing at least one carbon-carbon double bond, where the at least one carbon-carbon double bond occurs between the alpha and beta carbons of the chain. Terminal olefins may be represented by the formula: $H_2C=CH-R^*$, wherein each $R^*$ is independently, hydrogen or a $C_1$ to $C_{30}$ hydrocarbyl, preferably a $C_2$ to $C_{20}$ hydrocarbyl, preferably a $C_2$ to $C_{12}$ hydrocarbyl, preferably methyl, ethyl, propyl, butyl, pentyl, hexyl, and substituted and cyclic analogs thereof. For example, 1-hexene, 1-heptene, and 1-decene are terminal olefins that are particularly useful in embodiments herein.

In other embodiments, internal olefins may be used. For the purposes of this invention and the claims thereto, the term "internal olefin" refers to an organic compound containing at least one carbon-carbon double bond, where the at least one carbon-carbon double bond does not occur between the alpha and beta carbons of the chain. Internal olefins may be represented by the formula: $R^*HC=CH-R^*$, wherein each $R^*$ is independently, a $C_1$ to $C_{30}$ hydrocarbyl, preferably a $C_2$ to $C_{20}$ hydrocarbyl, preferably a $C_2$ to $C_{12}$ hydrocarbyl, preferably methyl, ethyl, propyl, butyl, pentyl, hexyl, and substituted and cyclic analogs thereof. For example, hex-2-ene, hept-3-ene, and TBS-protected 4-penten-1-ol (TBS means "tert-butyl silyl") are particularly useful in embodiments herein.

ROCM Metathesis Products

In such embodiments, the metathesis product comprises a mixture of the ROCM products of the cyclic olefin and the second olefinic reactant. The wide synthetic availability of cyclic olefins makes this route attractive, and cyclic compounds are particularly important in synthesis. Most significantly, ring systems are key to stereochemical control; the understanding of ring conformation often presents the most expeditious route for stereocenter installation. The ability to take these general carbocycles to highly functionalized linear molecules (which, ideally, would have differentially protected termini) is useful to the synthetic chemist.

ROCM involves a tandem sequence in which a cyclic olefin is opened and a second, acyclic olefin is crossed onto the newly formed termini. After the initial ring opening event, the Group 8 metal-bound intermediate has two options: reaction with another cyclic olefin or reaction with the other olefin. It will be appreciated that a ROCM reaction between a cyclic olefin and a second olefin reactant can result in several different types of reaction products, depending, in large part, on the relative rates of the ring-opening metathesis reaction and the cross-metathesis reaction between the second olefinic reactant and the cyclic olefin, as shown in FIG. 1, where n=1 to 100,000 and R is a $C_1$ to $C_{30}$ hydrocarbyl derived from the second olefin, preferably a $C_2$ to $C_{20}$ hydrocarbyl, preferably a $C_2$ to $C_{12}$ hydrocarbyl, preferably methyl, ethyl, propyl, butyl, pentyl, hexyl, and substituted and cyclic analogs thereof.

Accordingly, a cyclic olefin will undergo a ring opening reaction in the presence of the catalyst at a rate constant $k_{RO}$, and the second olefin reactant will undergo a cross-metathesis reaction with the ring opened cyclic olefin at a rate constant $k_{CM}$. When $k_{CM}$ is greater than or equal to $k_{RO}$, the ROCM product is predominantly a monomer, dimer, and/or oligomer. More specifically, when $k_{CM}$ is approximately equal to $k_{RO}$, the ROCM product is predominantly a dimer or oligomer, while when $k_{RO}$ is greater than $k_{CM}$, the ROCM product is predominantly a polymer. Dimers and oligomers are of particular interest because their internal olefin moieties may be further functionalized by metathesis or other transformations.

Monomers are also of interest, particularly when they can be prepared so as to be end differentiated, i.e., asymmetric with regard to the two terminal olefinic groups resulting from the ROCM reaction. It should be appreciated that $k_{RO}$ will be higher for moderately and highly strained cyclic olefins such as cyclooctadiene, but lower for low-strain olefins such as cyclopentene and cyclohexene.

The inventors have noted that when $k_{RO} \ll k_{CM}$ for a ROCM reaction, the metathesis reaction proceeds selectively towards the ROCM dimer product (see FIG. 1). FIG. 1 shows the possible outcomes of a ROCM reaction. The inventive catalysts demonstrate remarkable selectivity towards the ROCM dimer product, as measured by gas chromatography (GC). Yields of metathesis product were calculated from the data recorded on an Agilent 6890 GC spectrometer. Typically, a sample of the metathesis product will be taken and analyzed by GC. An internal standard, usually tetradecane, is used to derive the amount of metathesis product that is obtained. The amount of metathesis product is calculated from the area under the desired peak on the GC trace, relative to the internal standard. Yield or conversion is reported as a molar percentage and defined as 100×[moles of metathesis products obtained by GC]/[moles of feed material weighed into reaction vessel].

The choice of the cyclic olefin and the second olefin used in a ROCM reaction may allow for tailoring of the resultant capped poly(cyclic olefin). Use of olefins with protected functionalities, for example TBS-protected 4-penten-1-ol may allow for introduction of functional groups to the capped poly(cyclic olefin). Some examples of functionalized poly (cyclic olefin)s include those that are functionalized with maleic acid or maleic anhydride groups.

The functionalized capped poly(cyclic olefin) can in turn be derivatized with a derivatizing compound, such as described in U.S. Pat. No. 6,022,929; A. Toyota, T. Tsutsui, and N. Kashiwa, Polymer Bulletin 48, 213-219, 2002; and J. Am. Chem. Soc., 1990, 112, 7433-7434. The derivatizing compound can react with the functional groups of the functionalized capped poly(cyclic olefin) by any means known in the art, such as nucleophilic substitution, Mannich Base condensation, and the like. The derivatizing compound can be polar and/or contain reactive derivative groups. Preferred derivatizing compounds are selected from hydroxy containing compounds, amines, metal salts, anhydride containing compounds, and acetyl halide containing compounds. The derivatizing compounds can comprise at least one nucleophilic group and preferably at least two nucleophilic groups. An exemplary derivatized capped poly(cyclic olefin) may be made by contacting a functionalized capped poly(cyclic olefin), for example, one substituted with a carboxylic acid/anhydride or ester, with a nucleophilic reagent, for example, amines, alcohols (including polyols), amino alcohols, reactive metal compounds, and the like. (For more information please see U.S. Pat. No. 6,022,929, column 33, line 27 to column 74, line 63.)

ROMP Reactions

Other particular embodiments herein, relate to processes wherein the metathesis reaction is a ring opening metathesis polymerization reaction comprising: (i) contacting a cyclic olefin and a second olefinic reactant in the presence of the Group 8 metathesis catalyst described above under conditions and for a time period sufficient to allow the ring opening metathesis polymerization reaction to occur; and (ii) obtaining a ring opening metathesis polymerization product.

Metathesis Products

The cyclic olefins discussed above may undergo ROMP to form a polyolefin. The ROMP reaction may occur either in the presence or absence of solvent and may optionally include additives. Known additives include antistatics, antioxidants, light stabilizers, plasticizers, dyes, pigments, fillers, reinforcing fibers, lubricants, adhesion promoters, viscosity-increasing agents, and demolding enhancers. Illustrative examples of fillers for improving the optical physical, mechanical, and electrical properties include glass and quartz in the form of powders, beads and fibers, metal and semi-metal oxides, carbonates (i.e., $MgCO_3$, $CaCO_3$), dolomite, metal sulfates (such as, gypsum and barite), natural and synthetic silicates (i.e., zeolites, wollastonite, feldspars), carbon fibers, and plastic fibers or powders.

Metathesis Reactions to Produce LAOs

Yet other particular embodiments involve a process for performing a metathesis reaction, as described above, wherein the two or more olefins comprise at least one lower olefin and at least one renewable feedstream. In such embodiments, the metathesis product comprises a linear alphaolefin (LAO), preferably having 6 to 50 carbon atoms, preferably 8 to 30 carbon atoms.

a. Lower Olefins

For purposes of this invention and the claims thereto, the term "lower olefin" refers to an organic compound containing at least one carbon-carbon double bond and having 6 carbon atoms or less. Lower olefins are represented by the formula: $R^*$—$HC$=$CH$—$R^*$, wherein each $R^*$ is independently, hydrogen or a $C_1$ to $C_2$ hydrocarbyl, preferably hydrogen, methyl, or ethyl, more preferably $R^*$ is hydrogen. In a preferred embodiment, both $R^*$ are the same, preferably both $R^*$ are hydrogen. For example, ethylene is a lower olefin that is particularly useful in embodiments herein.

Non-limiting examples of suitable lower olefins include ethylene, propylene, butene, butadiene, and isomers thereof Preferably, the lower olefin is ethylene.

b. Renewable Feedstreams

"Renewable feedstreams" as used herein, means starting materials that are derived from renewable sources. A source is considered renewable if it is replenished by natural means. Renewable feedstreams useful herein include fatty acids, fatty acid esters, natural oils, biodiesel, triacylglycerides, or mixtures thereof Natural Oils "Natural oils," as used herein, includes oils derived from biological sources, including animals, plants, algae, and fungi. Natural oils typically comprise mixtures of fatty acids and fatty acid esters, which are discussed below. These fatty acids often naturally occur as esters of three fatty acids and glycerol, known as triglycerides, also discussed below.

Natural oils useful herein preferably contain fatty acids and fatty acid esters with at least one site of unsaturation and include, but are not limited to, canola oil, corn oil, soybean oil, rapeseed oil, algae oil, peanut oil, mustard oil, sunflower oil, tung oil, tall oil, perilla oil, grapeseed oil, linseed oil, safflower oil, pumpkin oil, palm oil, Jatropha oil, high-oleic soybean oil, high-oleic safflower oil, high-oleic sunflower oil, mixtures of animal and vegetable fats and oils, beef tallow, castor bean oil, dehydrated castor bean oil, cucumber oil, poppyseed oil, flaxseed oil, lesquerella oil, walnut oil, cottonseed oil, meadowfoam, tuna oil, sesame oils, waste oils/greases, and mixtures thereof.

While readily available vegetable oils are preferred sources of fatty acids for practicing disclosed embodiments of the present process, fatty acids and fatty acid esters available from animal fats including, without limitation, lard and fish oils, such as sardine oil, tuna oil, herring oil, and the like may be employed in embodiments herein. Furthermore, particular fatty acids or fatty acid precursors may also be advantageously available from genetically modified organisms, such as genetically modified plants, particularly genetically modified algae. Such genetically modified organisms are typically designed to produce a desired fatty acid or fatty acid precursor biosynthetically or to advantageously produce increased amounts of such compounds. Preferred natural oils include palm oil, soybean oil, sunflower oil, canola oil, Jatropha oil, and algae oil.

Fatty Acids and Fatty Acid Esters

Fatty acids are carboxylic acids with saturated or unsaturated aliphatic tails that occur naturally in many different natural oils. Fatty acid esters are alkyl esters of fatty acids, preferably $C_1$ to $C_{12}$ esters, preferably $C_1$ to $C_5$ esters, preferably methyl, ethyl, n-propyl, n-butyl esters, more preferably methyl or ethyl esters. An unsaturated fatty acid comprises a long carbon chain containing at least one carbon-carbon double bond and terminating in a carboxylic acid group. An unsaturated fatty acid ester also comprises a long carbon chain containing at least one carbon-carbon double bond but terminates in a carboxylate group.

Unsaturated fatty acids, unsaturated fatty acid esters, and mixtures thereof are of particular importance in embodiments herein. Any unsaturated fatty acid or fatty acid ester may be suitably employed to produce LAOS, provided that the unsaturated fatty acid or fatty acid ester can be metathesized in the manner disclosed herein. At least one carbon-carbon double bond may occur at any internal location, usually about the middle of the aliphatic tail. A terminal carbon-carbon double bond, at the opposite end of the carbon chain relative to the carboxylic acid or carboxylate group, is also suitably employed, although terminal carbon-carbon double bonds occur less commonly in fatty acids.

Monounsaturated fatty acids and fatty acid esters contain one carbon-carbon double bond in the long aliphatic tail. Examples of monounsaturated fatty acids and fatty acid esters useful herein include myristoleic acid, palmitoleic acid, sapienic acid, oleic acid, erucic acid, and alkyl esters thereof. Polyunsaturated fatty acids and fatty acid esters contain two or more carbon-carbon double bonds in the long aliphatic tail. Examples of polyunsaturated fatty acids and esters useful herein include linoleic acid, linolenic acid, arachidonic acid, eicosapentaenoic acid, docosahexaenoic acid, and alkyl esters thereof. Some natural oils may contain fatty acids and fatty acid esters that are polyunsaturated, and some of the sites of unsaturation may be internal. For instance, oleic acid, linoleic acid, and linolenic acid, and their respective esters are examples of fatty acid and fatty acid esters with internal sites of unsaturation. Methyl oleate has one internal double bond, methyl linoleate has two internal double bonds, and methyl linolenoate has three internal double bonds, as shown below.

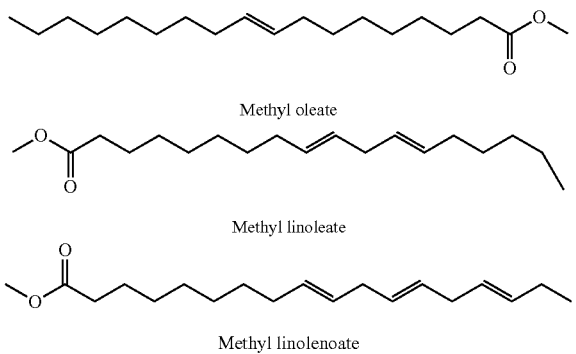

Methyl oleate

Methyl linoleate

Methyl linolenoate

Fatty acids and fatty acid esters useful herein include monounsaturated fatty acids and esters thereof, polyunsaturated fatty acids and esters thereof, and mixtures of monounsaturated and polyunsaturated fatty acids and esters thereof.

Typically, the unsaturated fatty acid will contain greater than 8 carbon atoms, preferably, greater than 10 carbon atoms, and more preferably, greater than 12 carbon atoms. Typically, the unsaturated fatty acid will contain less than 50 carbon atoms, preferably, less than 35 carbon atoms, and less than 25 carbon atoms.

The unsaturated fatty acid may be straight or branched and may be substituted along the fatty acid chain with one or more substituents, provided that the one or more substituents are substantially inert with respect to the metathesis process. Non-limiting examples of suitable substituents include alkyl moieties, preferably $C_{1-10}$ alkyl moieties, including, for example, methyl, ethyl, propyl, butyl, and the like; cycloalkyl moieties, preferably $C_{4-8}$ cycloalkyl moieties, including for example, cyclobutyl, cyclopentyl, cyclohexyl, and cyclooctyl; monocyclic aromatic moieties, preferably $C_6$ aromatic moieties, including for example, phenyl; and alkylaryl moieties, preferably $C_{7-16}$ alkylaryl moieties, including, for example, tolyl, ethylphenyl, xylyl, and the like; as well as hydroxyl, ether, keto, aldehyde, and halide, preferably, chloride and bromide functionalities.

Non-limiting examples of suitable unsaturated fatty acid and fatty acid esters include 3-hexenoic (hydrosorbic), trans-2-heptenoic, 2-octenoic, 2-nonenoic, cis-and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (gadoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), and like acids and corresponding esters thereof. Particularly preferred fatty acids and fatty acid esters useful herein include oleic acid, linoleic acid, linolenic acid, and esters thereof.

The natural oils useful in the processes described herein typically include a mixture of saturated (Cn:0), monounsaturated (Cn:1), and polyunsaturated (Cn:2, 3, etc.) fatty acids, where n is the number of carbon atoms present in the fatty acid (typically 8 to 50). For example, the fatty acid profiles of several potential natural oil feedstreams are shown in Table 1, below.

TABLE 1

Fatty Acid Profile of Several Typical Natural Oils

| Fatty Acid | Wt % | | | | |
|---|---|---|---|---|---|
| | Palm | Soybean | Sunflower | Canola | Jatropha |
| Myrisitic (C14:0) | 1.1 | 0.1 | 0 | 0 | 0.1 |
| Palmitic (C16:0) | 44 | 11.0 | 0 | 3.9 | 14.2 |
| Stearic (C18:0) | 4.5 | 4.0 | 4.5 | 1.9 | 7 |
| Oleic (C18:1) | 39.2 | 23.4 | 21.1 | 64.1 | 44.7 |
| Linoleic (C18:2) | 10.1 | 53.2 | 66.2 | 18.7 | 32.8 |
| Linolenic (C18:3) | 0.4 | 7.8 | 0 | 9.2 | 0.2 |
| Arachidic (C20:0) | 0 | 0 | 0.3 | 0.6 | 0.2 |
| Miscellaneous | 0.7 | 0.5 | 7.9 | 1.6 | 0.8 |

In a preferred embodiment, the renewable feedstream used herein comprises a combination of natural oils. Preferred combinations include two or more of tall oil, palm oil, tallow, waste grease, rapeseed oil, canola oil, soybean oil, sunflower oil, Jatropha oil, and algae oil. Alternate useful combinations include two (three or four) or more of soybean oil, sunflower oil, palm oil, canola oil, rapeseed oil, algae oil, Jatropha oil, and tallow.

Triacylglycerides (TAGs)

The chief constituent of natural oils is triacylglycerides (TAGs), also called triglycerides. TAGs are a naturally occurring ester of three fatty acids and glycerol. The three fatty acids can be all different, all the same, or only two the same. They can be saturated or unsaturated fatty acids, and the saturated fatty acids may have one or multiple sites of unsaturations. Chain lengths of the fatty acids in naturally occurring TAGs can be of varying lengths but 16, 18, and 20 carbons are the most common. Natural fatty acids found in plants and animals are typically composed of even numbers of carbon atoms due to the way they are bio-synthesized. Most natural fats contain a complex mixture of individual triglycerides and because of this, they melt over a broad range of temperatures.

TAGs typically have the chemical structure:

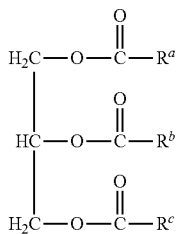

where $R^a$, $R^b$, and $R^c$ each, independently, represent a saturated or non-saturated hydrocarbon chain (preferably $R^a$, $R^b$, and $R^c$ each, independently, are a $C_{12}$ to $C_{28}$ alkyl or olefin, preferably $C_{16}$ to $C_{22}$ alkyl or olefin).

Different vegetable oils have different fatty acid profiles, with the same or different fatty acids occurring on a single glycerol. For example, an oil can have linoleic, oleic, and stearic acids attached to the same glycerol, with each of $R^a$, $R^b$, and $R^c$ representing one of these three fatty acids. In another example, there can be two oleic acids and one stearic acid attached to the same glycerol, each of $R^a$, $R^b$, and $R^c$ representing one of these fatty acids.

In one embodiment, a useful TAG consists of three unsaturated fatty acids, where at least one fatty acid is oleic acid. In another embodiment, a useful TAG consists of three unsaturated fatty acids, where at least one fatty acid is linoleic acid. In yet another embodiment, a useful TAG consists of three unsaturated fatty acids, where at least one fatty acid is oleic acid and at least one fatty acid is linoleic acid. In other embodiments, a mixture of different TAGs may be used.

Other materials containing fatty acid glycerides or other fatty acid esters can also be used, including phospholipids, lysophospholipids, and fatty acid wax esters. The free fatty acid content of useful natural oils is preferably about 0.1 wt % or less when employed in a basic homogeneous catalyst esterification reaction. Higher levels can be utilized as well, and levels up to about 3.0 wt %, or even as high as about 15.0 wt % or more may be tolerated.

TAGs may be processed by transesterification with alcohols to give biodiesel. Biodiesel is typically a mixture of mono-alkyl fatty acid esters, and is useful as a renewable feedstream for methods disclosed herein. The processing of natural oils is discussed in greater detail below.

Processing of Renewable Feedstreams

Raw or unrefined oils can be used in certain embodiments. However, filtered and refined oils are typically preferred. Use of degummed and filtered feedstreams minimizes the potential for emulsification and blockage in the reactor systems. Feedstreams with high water content can be dried before use. Feedstreams with high free fatty acid content can be passed through an esterification process to reduce the free fatty acid content before the process of esterification to convert fatty acid glycerides to monoalkyl esters. The reduction of free fatty acids and the conversion of fatty acid glycerides can be accomplished in the same processing step. Feedstreams containing other organic compounds (such as hexane, heptane, isohexane, etc.) can typically be processed without significant modifications to the reactor system.

In certain embodiments, processed oils, such as blown oils, are the source of fatty acids useful herein. Blown oils are processed through partial oxidation. Common blown oils available include linseed oil, castor oil, fish oil, and soybean oil.

Natural oils may be further processed before use in the present invention, for example, natural oils may be esterified with alcohols to covert any fatty acids present to fatty acid esters, to produce biodiesel. Biodiesel is a mixture of mono-alkyl fatty acid esters typically derived from the transesterification of natural oils and alcohols. While natural oils and alcohols are commonly employed as reactants in esterification reactions, any fatty acid source, such as free fatty acids, soaps, esters, glycerides (mono-, di-, and tri-), phospholipids, lysophospholipids, or amides, and a monohydric alcohol source, such as an alcohol, can be esterified.

Biodiesel compositions that are particularly useful in this invention are those which have high concentrations of oleic acids, erucic acids, and esters thereof. These fatty acids and esters have one site of unsaturation such that CM with ethylene yields the LAO, 1-decene, as the coproduct. Preferred biodiesel compositions are those produced from natural oils, such as canola oil, rapeseed oil, palm oil, and other high oleic or high erucic oils. Particularly preferred natural oils include those having at least 30 mol % combined oleic and erucic fatty acid or esters of all fatty acid and fatty acid esters combined, preferably at least 40%, preferably at least 50%, preferably at least 60%, preferably at least 70%, preferably at least 80%, preferably at least 90%.

In yet other embodiments, biodiesel compositions that are particularly useful in this invention are those which have high concentrations of oleic, erucic, linoleic, and linolenic acids and respective esters thereof. Preferred biodiesel compositions are those produced from vegetable oils such as canola oil, soybean oil, sunflower oil, Jatropha oil, and other oils having a high concentration of oleic, erucic, linoleic, and linolenic acids and respective esters thereof. Particularly preferred vegetable oils include those having at least 50 mol % oleic, erucic, linoleic, and linolenic acids and respective esters thereof of all fatty acid and fatty acid ester chains combined, preferably at least 60%, preferably at least 70%, preferably at least 80%, preferably at least 90%.

c. Linear AlphaOlefins (LAOS)

The metathesis catalyst may be combined with the lower olefin and renewable feedstream in any manner known in the art. In one embodiment, the metathesis catalysts described herein may be combined directly with the lower olefin and renewable feedstreams to produce alpha-olefins, preferably LAOS, preferably $C_4$ to $C_{24}$ alpha-olefins, preferably $C_4$ to $C_{24}$ LAOS, such as preferably 1-decene, 1-heptene, and/or 1-butene.

Typically, the molar ratio of lower olefin to renewable feedstream (such as unsaturated fatty acid or fatty acid ester) is greater than 0.8:1.0, preferably, greater than 0.9:1.0, greater than 1.0:1.0, greater than 1.5:1.0, greater than 2.0:1.0. Typically, the molar ratio of lower olefin to feed material (such as unsaturated fatty acid or fatty acid ester) is less than 3.0:1.0, preferably, less than 2.0:1.0, less than 1.5:1.0. Depending upon the specific reagents, other molar ratios may also be suitable. When the lower olefin is ethylene, for example, a significantly higher molar ratio can be used, because the self-metathesis of ethylene produces only ethylene again and therefore no undesirable co-product olefins are formed.

Accordingly, the molar ratio of ethylene to renewable feedstream may range from greater than 0.8:1 to typically less than 20:1.

Generally, the renewable feedstream comprises unsaturated fatty acid esters and/or unsaturated fatty acids and is provided as a liquid at the process temperature, and it is generally preferred to be used neat, that is, without a diluent or solvent. The use of a solvent usually increases recycle requirements and increases costs. Optionally, however, if desired, a solvent can be employed with the lower olefin and/or renewable feedstream. A solvent may be desirable, for instance, where liquid feed material and lower olefin are not entirely miscible, and both then can be solubilized in a suitable solvent. In certain embodiments, the CM reaction reactions of the lower olefin and the renewable feedstream may be run in a biphasic mixture of solvents, in an emulsion or suspension, or in a lipid vesicle or bilayer.

Suitable diluents/solvents for the process include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof, including those that can be found commercially (Isopar™); perhalogenated hydrocarbons such as perfluorinated $C_{4-10}$ alkanes, chlorobenzene, and aromatic and alkylsubstituted aromatic compounds, such as benzene, toluene, mesitylene, and xylene. Suitable diluents/solvents also include aromatic hydrocarbons, such as toluene or xylenes, and chlorinated solvents, such as dichloromethane. In a preferred embodiment, the feed for the process comprises 60 vol % solvent or less, based on the total volume of the feed, preferably 40 vol % or less, preferably 20 vol % or less.

The quantity of metathesis catalyst that is employed in the process of this invention is any quantity that provides for an operable metathesis reaction. Preferably, the ratio of moles of renewable feedstream (such as unsaturated fatty acid or fatty acid ester) to moles of metathesis catalyst is typically greater than 10:1, preferably greater than 100:1, preferably greater than 1,000:1, preferably greater than 10,000:1, preferably greater than 25,000:1, preferably greater than 50,000:1, preferably greater than 100,000:1.

In a preferred embodiment, from 0.005 nmoles to 500 nmoles, preferably from 0.1 to 250 nmoles, and most preferably from 1 to 50 nmoles of the metathesis catalyst are charged to the reactor per 3 mmoles of renewable feedstream (such as TAGs, biodiesel, fatty acids, fatty acid esters, and/or fatty acid alkyl esters or mixtures thereof, preferably fatty acid esters) charged.

The process may be batch, semi-batch, or continuous. As used herein, the term continuous means a system that operates without interruption or cessation. For example, a continuous process to produce a metathesis product would be one where the reactants are continually introduced into one or more reactors and metathesis products are continually withdrawn.

The processes may be conducted in any of glass lined, stainless steel, or similar type reaction equipment. Useful reaction vessels include reactors (including continuous stirred tank reactors, batch reactors, reactive extruder, pipe, or pump, continuous flow fixed bed reactors, slurry reactors, fluidized bed reactors, and catalytic distillation reactors). The reaction zone may be fitted with one or more internal and/or external heat exchanger(s) in order to control temperature fluctuations.

If the process is conducted in a batch reactor, then the contacting time of the renewable feedstream and catalyst can be of any duration, provided that the desired olefin metathesis products are obtained. Generally, the contacting time in a reactor is greater than 5 minutes, and preferably greater than 10 minutes. Generally, the contacting time in a reactor is less than 25 hours, preferably less than 15 hours, and more preferably less than 10 hours.

In a preferred embodiment, the reactants (for example, metathesis catalyst; renewable feedstream; lower olefin, optional diluent, etc.) are combined in a reaction vessel at a temperature of 20° C. to 300° C. (preferably 20° C. to 200° C., preferably 30° C. to 100° C., preferably 40° C. to 60° C.) and an olefin (such as ethylene) at a pressure of 0.1 psig to 1000 psi (0.7 kPa to 6.9 MPa) (preferably 20 psi to 400 psi (0.14 MPa to 2.8 MPa), preferably 50 psi to 250 psi (0.34 MPa to 1.7 MPa)), if the olefin is present, for a residence time of 0.5 seconds to 48 hours (preferably 0.25 seconds to 5 hours, preferably 30 minutes to 2 hours).

In certain embodiments, where the olefin is a gaseous olefin, the olefin pressure is greater than 5 psig (34.5 kPa), preferably, greater than 10 psig (68.9 kPa), and more preferably, greater than 45 psig (310 kPa). When a diluent is used with the gaseous olefin, the aforementioned pressure ranges may also be suitably employed as the total pressure of olefin and diluent. Likewise, when a liquid olefin is employed and the process is conducted under an inert gaseous atmosphere, then the aforementioned pressure ranges may be suitably employed for the inert gas pressure.

In a preferred embodiment, the process is typically a solution process, although it may be a bulk or high pressure process. Homogeneous processes are preferred. (A homogeneous process is defined to be a process where at least 90 wt % of the product is soluble in the reaction media.) A bulk homogeneous process is particularly preferred. (A bulk process is defined to be a process where reactant concentration in all feeds to the reactor is 70 vol % or more.) Alternately, no solvent or diluent is present or added in the reaction medium (except for the small amounts used as the carrier for the catalyst or other additives or amounts typically found with the reactants, e.g., propane in propylene).

In the process of this invention, the conversion of the renewable feedstream (preferably fatty acid ester) to the desired LAO products can vary widely depending upon the specific reagents, such as, for example, the lower olefins, the specific metathesis catalyst, the specific process conditions employed, and the specific chemical makeup of the fatty acid ester. For the purpose of this invention, "conversion" is defined as the mole percentage of feed material that is converted to the CM products, that is, LAOS. In some embodiments, the conversion of the renewable feedstream (preferably fatty acid ester) to LAOs is greater than 50 mol %, preferably, greater than 60 mol %, and more preferably, greater than 70 mol %. In other embodiments, the conversion of the renewable feedstream (preferably fatty acid ester) to LAOs is greater than 50 mol %, preferably, greater than 60 mol %, and more preferably, greater than 70 mol %.

In the process of this invention, the yields of the LAO can also vary depending upon the specific reagent olefins, catalyst, and process conditions employed. For the purposes of this invention, "yield" will be defined as the mole percentage of product (such as LAOs) formed relative to the initial moles of renewable feedstream (such as fatty acid ester in the feed). In embodiments where the renewable feedstock comprises TAGs (as represented in the formula below):

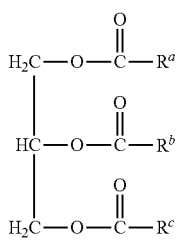

where $R^a$, $R^b$, and $R^c$ each, independently, represent a saturated or unsaturated hydrocarbon chain (preferably $R^a$, $R^b$, and $R^c$ each, independently, are a $C_{12}$ to $C_{28}$ alkyl or olefin, preferably $C_{16}$ to $C_{22}$ alkyl or olefin), the yield may be defined as defined by the mole percentage of LAOs formed relative to the initial moles of starting fatty acid ester (unsaturated $R^a$+moles of unsaturated $R^b$+moles of unsaturated $R^c$) introduced into the reactor. Alternatively, the yield may be defined by the mole percentage of LAOs formed relative to the initial moles of starting fatty acid ester. In some embodiments, the yield of LAOs is greater than 30 mol % or more, preferably greater than 35 mol % or more, preferably greater than 40 mol % or more, preferably greater than 45 mol % or more, preferably greater than 50 mol % or more, preferably greater than 55 mol % or more, preferably greater than 60 mol % or more. In some embodiments, the yield of LAOs is greater than 30 mol % or more, preferably greater than 35 mol % or more, preferably greater than 40 mol % or more, preferably greater than 45 mol % or more, preferably greater than 50 mol % or more, preferably greater than 55 mol % or more, preferably greater than 60 mol % or more.

For the purposes of this invention, "productivity" is defined to be the amount in grams of product (such as LAO) produced per mmol of catalyst introduced into the reactor, per hour. In a preferred embodiment, the productivity of the process is at least 200 g of LAO (such as decene-1) per mmol of catalyst per hour, preferably at least 5000 g/mmol/hour, preferably at least 10,000 g/mmol/hour, preferably at least 300,000 g/mmol/hour.

For the purposes of this invention, "selectivity" is a measure of conversion of lower olefin and renewable feedstream to the LAO products, and is defined by the mole percentage of LAOs formed relative to the initial moles of lower olefin or renewable feedstream. In a preferred embodiment, the selectivity of the process is at least 20 wt % LAOS, based upon the weight of the material exiting the reactor, preferably at least 25 wt %, preferably at least 30 wt %, preferably at least 35 wt %, preferably at least 40 wt %, preferably at least 45 wt %, preferably at least 50 wt %, preferably at least 60 wt %, preferably at least 70 wt %, preferably at least 80 wt %, preferably at least 85 wt %, preferably at least 90 wt %, preferably at least 95 wt %.

For the purpose of this invention, "catalyst turnover number" (TON) is a measure of how active the catalyst compound is and is defined as the number of moles of LAO formed per mole of catalyst compound. In a preferred embodiment, the (TON) of the process is at least 5,000, preferably at least 10,000, preferably at least 50,000, preferably at least 100,000, preferably at least 1,000,000.

In a particular embodiment, a fatty acid or a fatty acid ester which is monosaturated may be cross-metathesized with a lower olefin in the presence of metathesis catalysts of the present invention to produce a desired $C_4$ to $C_{40}$ LAO. For example, methyl oleate and ethylene may be cross-metathesized using a suitable metathesis catalyst to produce major CM products of 1-decene and methyl-9-decanoate. Both products are alpha-olefins, however the decanoate terminates in an ester moiety at the opposite end of the chain from the carbon-carbon double bond. In addition to the major products, the methyl oleate may self-metathesize to produce small amounts of 9-octadecene, a less desirable product, and dimethyl-9-octadecene-1,18-dioate, a second less desirable product.

In yet other embodiments, mixtures of fatty acids, or fatty acid esters, or a natural oil comprising mixtures of monosaturated and polyunsaturated fatty acids and/or esters, or a mixture of natural oils may be cross-metathesized with a lower olefin in the presence of a suitable metathesis catalyst to produce a desired LAO. For example, a mixture of methyl oleate and methyl linoleate may be cross-metathesized with ethylene to produce 1-decene.

In another embodiment, this invention relates to:

1. A metathesis catalyst comprising a Group 8 metal complex represented by the formula:

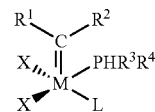

wherein:

M is a Group 8 metal (preferably M is ruthenium or osmium, preferably ruthenium);

each X is independently an anionic ligand (preferably selected from the group consisting of halides, alkoxides, aryloxides, and alkyl sulfonates, preferably a halide, preferably chloride);

$R^1$ and $R^2$ are independently selected from the group consisting of hydrogen, a $C_1$ to $C_{30}$ hydrocarbyl, and a $C_1$ to $C_{30}$ substituted hydrocarbyl;

$R^3$ and $R^4$ are independently selected from the group consisting of hydrogen, $C_1$ to $C_{12}$ hydrocarbyl groups, substituted $C_1$ to $C_{12}$ hydrocarbyl groups, and halides (preferably $R^3$ and $R^4$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl); and L is a neutral donor ligand, preferably L is selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; preferably a phosphine, a sulfonated phosphine, an N-heterocyclic carbene, a cyclic alkyl amino carbene, and substituted analogs thereof (preferably L is selected from a phosphine, an N-heterocyclic carbene, a cyclic alkyl amino carbene, and substituted analogs thereof).

2. The metathesis catalyst of paragraph 1, represented by the formula:

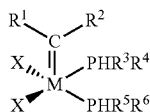

wherein:
M is a Group 8 metal (preferably M is ruthenium or osmium, preferably ruthenium);
each X is independently an anionic ligand (preferably selected from the group consisting of halides, alkoxides, aryloxides, and alkyl sulfonates, preferably a halide, preferably chloride); $R^1$ and $R^2$ are independently selected from the group consisting of hydrogen, a $C_1$ to $C_{30}$ hydrocarbyl, and a $C_1$ to $C_{30}$ substituted hydrocarbyl; and
$R^3$, $R^4$, $R^5$, and $R^6$ are independently selected from the group consisting of hydrogen, $C_1$ to $C_{12}$ hydrocarbyl groups, substituted $C_1$ to $C_{12}$ hydrocarbyl groups, and halides (preferably $R^3$, $R^4$, $R^5$, and $R^6$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl), (alternately at least one of $R^3$ and $R^4$ and at least one of $R^5$ and $R^6$ are selected from the group consisting of $C_1$ to $C_{12}$ hydrocarbyl groups, substituted $C_1$ to $C_{12}$ hydrocarbyl groups, and halides), (alternately $R^3$ and $R^4$ may form a ring), (alternately $R^5$ and $R^6$ may form a ring), (alternately $R^3$ and at least one of $R^5$ and $R^6$ may form a ring), (alternately $R^4$ and at least one of $R^5$ and $R^6$ may form a ring).
3. The metathesis catalyst of paragraphs 1 to 2, wherein the Group 8 metal complex is selected from:
[(HP(tert-butyl)$_2$)$_2$Ru(C$_5$H$_8$)Cl$_2$],
[(H$_2$P(tert-butyl))$_2$Ru(C$_5$H$_8$)Cl$_2$],
[(HP(cyclohexyl)$_2$)$_2$Ru(C$_5$H$_8$)Cl$_2$],
[(H$_2$P(cyclohexyl))$_2$Ru(C$_5$H$_8$)Cl$_2$],
[(HP(cyclopentyl)$_2$)$_2$Ru(C$_5$H$_8$)Cl$_2$],
[(H$_2$P(cyclopentyl))$_2$Ru(C$_5$H$_8$)Cl$_2$],
[(HP(n-butyl)$_2$)$_2$Ru(C$_5$H$_8$)Cl$_2$],
[(H2P(n-butyl))$_2$RU(C$_5$H$_8$)Cl$_2$],
[(HP(sec-butyl)$_2$)$_2$Ru(C$_5$H$_8$)Cl$_2$],
[(H$_2$P(sec-butyl))$_2$Ru(C$_5$H$_8$)Cl$_2$], and
fluoride and bromide derivatives thereof (preferably. wherein the Cl$_2$ in the above list is replaced with F$_2$, Br$_2$, ClF, ClBr or FBr).
4. A process for performing a metathesis reaction comprising:
(i) contacting one or more olefins (preferably two or more olefins) with the metathesis catalyst of any of paragraphs 1 to 3; and
(ii) obtaining at least one metathesis product.
5. The process of paragraph 4, wherein the one or more olefins comprise at least one cyclic olefin (preferably the cyclic olefin is selected from cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, and norbornadiene).
6. The process of paragraph 4 to 5, wherein the one or more olefins comprise a second olefinic reactant (preferably the second olefinic reactant is selected from ethylene, propylene, butene, butadiene, pentene, hexene, heptene, octene, nonene, decene, undecene, and dodecene).
7. The process of paragraphs 4 to 6, wherein the one or more olefins comprise at least one renewable feedstream and at least one cyclic olefin (preferably the at least one renewable feedstream is selected from canola oil, corn oil, soybean oil, rapeseed oil, algae oil, peanut oil, mustard oil, sunflower oil, tung oil, tall oil, perilla oil, grapeseed oil, linseed oil, safflower oil, pumpkin oil, palm oil, Jatropha oil, high-oleic soybean oil, high-oleic safflower oil, high-oleic sunflower oil, mixtures of animal and vegetable fats and oils, beef tallow, castor bean oil, dehydrated castor bean oil, cucumber oil, poppyseed oil, flaxseed oil, lesquerella oil, walnut oil, cottonseed oil, meadowfoam, tuna oil, sesame oils, waste oils/greases and mixtures thereof, preferably the renewable feedstream is selected from palm oil, soybean oil, sunflower oil, canola oil, Jatropha oil, and algae oil).
8. The process of paragraphs 4 to 7, wherein the one or more olefins comprise at least one raffinate feedstream (preferably a $C_4$ and/or $C_5$ raffinate feed stream).
9. The process of paragraphs 4 to 8, wherein the metathesis reaction is a ring opening cross metathesis reaction comprising:
(i) contacting a cyclic olefin and a second olefinic reactant in the presence of the Group 8 metathesis catalyst under conditions and for a time period sufficient to allow the ring opening cross metathesis reaction to occur; and
(ii) obtaining a ring opening cross metathesis product (preferably the ring opening cross metathesis product is a dimer and is obtained in greater than 50 mol % yield, preferably is obtained in greater than 70 mol % yield).
10. The process of paragraphs 4 to 8, wherein the metathesis reaction is a ring opening metathesis polymerization reaction comprising:
(i) contacting a cyclic olefin and a second olefinic reactant in the presence of the Group 8 metathesis catalyst under conditions and for a time period sufficient to allow the ring opening metathesis polymerization reaction to occur; and
(ii) obtaining a ring opening metathesis polymerization product.
11. The metathesis catalyst of paragraphs 1 to 3 or the process of paragraphs 4 to 10, wherein the substituted hydrocarbyl is substituted with one or more of N, O, S, and P.

Experimental Section

For purposes of this invention and the claims thereto, Cy is cyclohexyl, DCM is dichloromethane, THF is tetrahydrofuran, tBu is tert-butyl, and DCPD is dicyclopentadiene.

Tests and Materials

Typical dry-box procedures for synthesis of air-sensitive compounds were followed, including using dried glassware (90° C., 4 hours) and using anhydrous solvents purchased from Sigma Aldrich (St. Louis, Mo.), which were further dried over 3 A sieves. All reagents were purchased from Sigma-Aldrich and used as received, unless otherwise noted. 1-hexene and 1-decene were obtained from Aldrich and dried over a NaK alloy prior to use.

$^1$H and $^{31}$P spectra were recorded on Bruker 250 and 500 spectrometers.

Products were analyzed by gas chromatography (Agilent 6890N with auto-injector) using helium as a carrier gas at 38 cm/sec. A column having a length of 60 m(J & W Scientific DB-1, 60 m×0.25 mm I.D.×1.0 μm film thickness) packed with a flame ionization detector (FID), an Injector temperature of 250° C., and a Detector temperature of 250° C. were used. The sample injected into the column in an oven at 70° C., then heated to 275° C. over 22 minutes (ramp rate 10° C./min to 100° C., 30° C./min to 275° C., hold).

Yields of metathesis product were calculated from the data recorded on an Agilent 6890 GC spectrometer. Typically, a sample of the metathesis product will be taken and analyzed by GC. An internal standard, usually tetradecane, is used to derive the amount of metathesis product that is obtained. The amount of metathesis product is calculated from the area under the desired peak on the GC trace, relative to the internal standard. Yield or conversion is reported as a percentage and defined as 100×[moles of metathesis products obtained by GC]/[moles of feed material weighed into reaction vessel].

EXAMPLES

Ring-Opening Cross Metathesis (ROCM)

Catalysts described herein were used for the ROCM of DCPD (dicyclopentadiene) or 5-ethylidene-2-norbornene (ENB or 5-ethylidene-2-bicyclo[2.2.1]hept-2-ene) with 1-decene or 1-hexene. The Group 8 metal complex used was $[(HP(tBu)_2Ru(C_5H_8)Cl_2]$ which was prepared as described below, and is represented by the formula below.

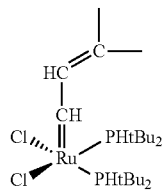

where t-Bu is t-butyl.
Catalyst Synthesis
Synthesis of (t-Bu$_2$PH)$_3$RuHCl

A 75 mL Fisher-Porter bottle was charged with [{RuCl$_2$(cod)}$_x$] (1.00 g, 3.57 mmol, where cod is cyclooctadiene), di-tert-butylphosphine (1.72 g, 11.8 mmol), triethylamine (0.361 g, 3.57 mmol), THF (25 mL), and a stir bar. The vessel was pressurized with hydrogen to 150 psi (1.03 MPa) and the reaction was stirred at 80° C. for 60 hours, with the pressure dropping to 90 psi (0.62 MPa). The reaction was allowed to cool to room temperature and depressurized, and white solids were filtered off. The remaining dark red solution was then dried in vacuo to a solid, which was then washed with cold methanol and dried in vacuo for 12 hours. Obtained 1.50 g, 69% yield.
Synthesis of [(HP(tBu)$_2$)$_2$Ru(C$_5$H$_8$)Cl$_2$]

(t-Bu$_2$P)$_3$RuHCl, (1.06 g, 1.74 mmol) was dissolved in toluene (40 mL) and cooled to −80° C. A solution of 3-chloro-3-methyl-1-butyne (0.375 g, 3.66 mmol) in toluene (5 mL) was added to the stirred solution. The solution was removed from the cold bath after 15 minutes and allowed to sit for 12 hours. Dark colored crystals had precipitated and the red-brown supernatant solution was decanted off. The crystals were then washed with four 20 mL portions of cold toluene and then dried in vacuo for 12 hours. Obtained 0.342 g of blue-green crystalline solid, 38% yield. $^{31}$P NMR (CD$_2$Cl$_2$), 400 MHz): δ=72.4 (s). The crystal structure of the catalyst is shown in FIG. 2.

Example 1

ROCM of Dicyclopentadiene (DCPD) and 1-decene
(Inventive)

Approximately 42.4 g of 1-decene was added to a 500-mL, 3-neck round bottom flask. Approximately 5 mg of a ruthenium catalyst [(HP(tBu)$_2$Ru(C$_5$H$_8$)Cl$_2$] was weighed and dissolved in 25 mL of dichloromethane. The catalyst solution was transferred to an addition funnel. Approximately 20 g of DCPD was weighed and dichloromethane was added to create a solution with a volume less than 50 mL. The solution was transferred to a second addition funnel. Approximately half of the catalyst solution was added to the 1-decene and immediately followed by a slow drip of DCPD. The reaction occurred in an oil bath set at 50° C. After the complete addition of DCPD, the remaining portion of the catalyst was added. A gas chromatograph (GC) sample was taken. The solution was left to stir at 50° C. for 48 hours. Approximately 1 g of silica was added to the product with 10 mL of dichloromethane to remove catalyst. The solution was filtered using a glass frit. Product was distilled using short path distillation with an oil bath temperature set to 200° C. 27.8 grams of oil were obtained. GC analysis indicated product contained 72 mol % C$_{20}$ (ROCM dimer product), 3 mol % C$_{18}$ (9-octadecene, homometathesis dimer product for 1-decene), and 17 mol %>C$_{20}$ (homometathesis product for DCPD plus ROCM oligomer products). The structure of the major product (the cross-metathesis dimer product) is shown below:

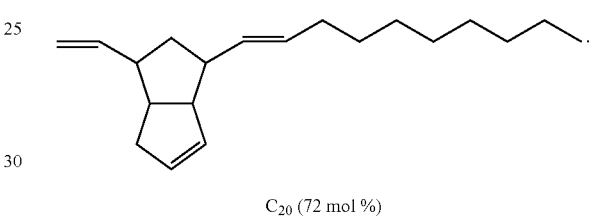

C$_{20}$ (72 mol %)

The inventors have surprisingly found that the Group 8 complexes disclosed herein, surprisingly produce the ROCM dimer product in greater than 70 mol % yield.

Example 2

ROCM of 5-Ethylidene-2-Norbornene and 1-hexene
(Inventive)

5 mg of [(HP(t-Bu)$_2$)$_2$Ru(C$_5$H$_8$)Cl$_2$] was dissolved in 1 mL of anhydrous, nitrogen-purged toluene. Approximately, 11.7 g of 1-hexene was added to the catalyst solution in a 500-mL, 3-neck round bottom flask equipped with stir bar. Approximately 50 g of ethylidenenorbornene (ENB) was added to the 1-hexene and Ru-catalyst in a dropwise manner using an addition funnel. The solution was allowed to sit overnight at room temperature. Approximately 10 mL of dichloromethane and less than 1 g of silica was added to the product. The solution was stirred for approximately four hours and then filtered using a glass frit with slight vacuum. The solids were discarded and the resulting solution was then placed in an oil bath at 60° C. overnight with a nitrogen purge. The percent conversion to the cross metathesis product was 65% by GC and this includes loss of product during transfer(s). The inventors have surprisingly found that the Group 8 complexes disclosed herein, surprisingly produce the ROCM dimer product in greater than 60 mol % yield.

Example 3

ROCM of DCPD and 1-decene (Comparative)

Approximately 42.4 g of 1-decene was added to a 3-neck, 500-mL round bottom flask. A solution of 1 mg/mL {[2-(i- propoxy)-5-(N,N-dimethyl-aminosulfonyl)phenyl]methylene} (1,3-bis (2,4,6-trimethylphenyl)-4,5-dihydroimidazol-2-ylidene)ruthenium dichloride catalyst was obtained. A volume of 5-mL of the ruthenium catalyst was measured and added to 25 mL of dichloromethane. The catalyst in dichloromethane was added to an addition funnel. Approximately 20 g of DCPD was weighed and solubilized using dichloromethane and placed into a second addition funnel. The total volume of DCPD and dichloromethane was less than 50 mL. The round bottom flask containing the 1-decene was placed in an oil bath at 50.5° C. (working temperature 50° C.-52° C.). At the start of the reaction, half of the catalyst in dichloromethane was added to the 1-decene. Immediately following the catalyst addition, DCPD was added drop-wise to the 1-decene. An additional 5.0 mL of 1-mg/mL catalyst was added and the reaction was maintained at 50° C. for approximately 24 hours. 26.5 grams of an oil was obtained. GC analysis indicated the product was a mixture of 18 mol % $C_{18}$ (9-octadecene, homometathesis product of 1-decene), 30 mol % $C_{20}$ (ROCM dimer of 1-decene and DCPD), and 50 mol %>$C_{20}$ (homometathesis product for DCPD plus ROCM oligomer products).

Here, the comparative catalyst was not selective for the ROCM dimer product, but instead produced the >$C_{20}$ (homometathesis product for DCPD plus ROCM oligomer products) as the major product. In contrast, the inventive catalyst produces the ROCM dimer as the major product.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise, "comprising" encompasses the terms "consisting essentially of," "is," and "consisting of" and anyplace "comprising" is used "consisting essentially of," "is," or "consisting of" may be substituted therefor.

We claim:

1. A metathesis catalyst comprising:
a Group 8 metal complex represented by the formula:

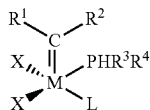

wherein:
M is a Group 8 metal;
each X is independently an anionic ligand;
$R^1$ and $R^2$ are independently selected from the group consisting of hydrogen, a $C_1$ to $C_{30}$ hydrocarbyl, and a $C_1$ to $C_{30}$ substituted hydrocarbyl;
$R^3$ and $R^4$ are independently selected from the group consisting of hydrogen, $C_1$ to $C_{12}$ hydrocarbyl groups, substituted $C_1$ to $C_{12}$ hydrocarbyl groups, and halides; and
L is a neutral donor ligand.

2. The metathesis catalyst of claim 1, wherein M is ruthenium or osmium.

3. The metathesis catalyst of claim 1, wherein X is selected from the group consisting of halides, alkoxides, aryloxides, and alkyl sulfonates.

4. The metathesis catalyst of claim 1, wherein X is a halide.

5. The metathesis catalyst of claim 1, wherein $R^3$ and $R^4$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

6. The metathesis catalyst of claim 1, wherein $R^3$ and $R^4$ are independently selected from the group consisting of hydrogen, methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

7. The metathesis catalyst of claim 1, wherein L is selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof.

8. The metathesis catalyst of claim 1, wherein L is selected from the group consisting of a phosphine, a sulfonated phosphine, an N-heterocyclic carbene, a cyclic alkyl amino carbene, and substituted analogs thereof.

9. The metathesis catalyst of claim 1, wherein $R^3$ and $R^4$ may form a ring.

10. The metathesis catalyst of claim 1, wherein the metathesis catalyst comprises a Group 8 metal complex represented by the formula:

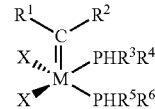

wherein:
M, X, $R^1$, $R^2$, $R^3$, and $R^4$ are as defined in claim 1; and
$R^5$ and $R^6$ are independently selected from the group consisting of hydrogen, $C_1$ to $C_{12}$ hydrocarbyl groups, substituted $C_1$ to $C_{12}$ hydrocarbyl groups, and halides.

11. The metathesis catalyst of claim 10, wherein at least one of $R^3$ and $R^4$ and at least one of $R^5$ and $R^6$ are selected from the group consisting of $C_1$ to $C_{12}$ hydrocarbyl groups, substituted $C_1$ to $C_{12}$ hydrocarbyl groups, and halides.

12. The metathesis catalyst of claim 10, wherein $R^5$ and $R^6$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

13. The metathesis catalyst of claim 10, wherein $R^5$ and $R^6$ are independently selected from the group consisting of hydrogen, methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

14. The metathesis catalyst of claim 10, wherein $R^5$ and $R^6$ may form a ring.

15. The metathesis catalyst of claim 10, wherein $R^3$ and at least one of $R^5$ and $R^6$ may form a ring.

16. The metathesis catalyst of claim 10, wherein $R^4$ and at least one of $R^5$ and $R^6$ may form a ring.

17. The metathesis catalyst of claim 1, wherein the Group 8 metal complex is selected from:
[(HP(tert-butyl)$_2$)$_2$Ru(C$_5$H$_8$)Cl$_2$],
[(H$_2$P(tert-butyl))$_2$Ru(C$_5$H$_8$)Cl$_2$],

[(HP(cyclohexyl)₂)₂Ru(C₅H₈)Cl₂],
[(H₂P(cyclohexyl))₂Ru(C₅H₈)Cl₂],
[(HP(cyclopentyl)₂)₂Ru(C₅H₈)Cl₂],
[(H₂P(cyclopentyl))₂Ru(C₅H₈)Cl₂],
[(HP(n-butyl)₂)₂Ru(C₅H₈)Cl₂],
[(H₂P(n-butyl))₂Ru(C₅H₈)Cl₂],
[(HP(sec-butyl)₂)₂Ru(C₅H₈)Cl₂],
[(H₂P(sec-butyl))₂Ru(C₅H₈)Cl₂], and
fluoride and bromide derivatives thereof.

18. A process for performing a metathesis reaction comprising:
(i) contacting one or more olefins with a metathesis catalyst;
wherein the metathesis catalyst comprises a Group 8 metal complex represented by the formula:

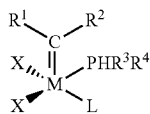

wherein:
M is a Group 8 metal;
each X is independently an anionic ligand;
$R^1$ and $R^2$ are independently selected from the group consisting of hydrogen, a $C_1$ to $C_{30}$ hydrocarbyl, and a $C_1$ to $C_{30}$ substituted hydrocarbyl;
$R^3$ and $R^4$ are independently selected from the group consisting of hydrogen, $C_1$ to $C_{12}$ hydrocarbyl groups, substituted $C_1$ to $C_{12}$ hydrocarbyl groups, and halides;
L is a neutral donor ligand; and
(ii) obtaining at least one metathesis product.

19. The process of claim 18, wherein M is ruthenium or osmium.

20. The process of claim 18, wherein X is selected from the group consisting of halides, alkoxides, aryloxides, and alkyl sulfonates.

21. The process of claim 18, wherein X is a halide.

22. The process of claim 18, wherein $R^3$ and $R^4$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

23. The process of claim 18, wherein $R^3$ and $R^4$ are independently selected from the group consisting of hydrogen, methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

24. The process of claim 18, wherein L is selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof.

25. The process of claim 18, wherein L is selected from the group consisting of a phosphine, a sulfonated phosphine, an N-heterocyclic carbene, a cyclic alkyl amino carbene, and substituted analogs thereof.

26. The process of claim 18, wherein $R^3$ and $R^4$ may form a ring.

27. The process of claim 18, wherein the metathesis catalyst comprises a Group 8 metal complex represented by the formula:

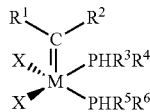

wherein:
M, X, $R^1$, $R^2$, $R^3$, and $R^4$ are as defined in claim 18; and
$R^5$ and $R^6$ are independently selected from the group consisting of hydrogen, $C_1$ to $C_{12}$ hydrocarbyl groups, substituted $C_1$ to $C_{12}$ hydrocarbyl groups, and halides.

28. The process of claim 27, wherein at least one of $R^3$ and $R^4$ and at least one of $R^5$ and $R^6$ are selected from the group consisting of $C_1$ to $C_{12}$ hydrocarbyl groups, substituted $C_1$ to $C_{12}$ hydrocarbyl groups, and halides.

29. The process of claim 27, wherein $R^5$ and $R^6$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

30. The process of claim 27, wherein $R^5$ and $R^6$ are independently selected from the group consisting of hydrogen, methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof.

31. The process of claim 27, wherein $R^5$ and $R^6$ may form a ring.

32. The process of claim 27, wherein $R^3$ and at least one of $R^5$ and $R^6$ may form a ring.

33. The process of claim 27, wherein $R^4$ and at least one of $R^5$ and $R^6$ may form a ring.

34. The process of claim 18, wherein the Group 8 metal complex is selected from:
[(HP(tert-butyl)₂)₂Ru(C₅H₈)Cl₂],
[(H₂P(tert-butyl))₂Ru(C₅H₈)Cl₂],
[(HP(cyclohexyl)₂)₂Ru(C₅H₈)Cl₂],
[(H₂P(cyclohexyl))₂Ru(C₅H₈)Cl₂],
[(HP(cyclopentyl)₂)₂Ru(C₅H₈)Cl₂],
[(H₂P(cyclopentyl))₂Ru(C₅H₈)Cl₂],
[(HP(n-butyl)₂)₂Ru(C₅H₈)Cl₂],
[(H₂P(n-butyl))₂Ru(C₅H₈)Cl₂],
[(HP(sec-butyl)₂)₂Ru(C₅H₈)Cl₂],
[(H₂P(sec-butyl))₂Ru(C₅H₈)Cl₂], and
fluoride and bromide derivatives thereof.

35. The process of claim 18, wherein the one or more olefins comprise at least one cyclic olefin.

36. The process of claim 35, wherein the cyclic olefin is selected from cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, and norbornadiene.

37. The process of claim 18, wherein the one or more olefins comprise a second olefinic reactant.

38. The process of claim 37, wherein the second olefinic reactant is selected from ethylene, propylene, butene, butadiene, pentene, hexene, heptene, octene, nonene, decene, undecene, and dodecene.

39. The process of claim 18, wherein the one or more olefins comprise at least one renewable feedstream and at least one cyclic olefin.

40. The process of claim 39, wherein the at least one renewable feedstream is selected from canola oil, corn oil, soybean oil, rapeseed oil, algae oil, peanut oil, mustard oil, sunflower oil, tung oil, tall oil, perilla oil, grapeseed oil, linseed oil, safflower oil, pumpkin oil, palm oil, Jatropha oil, high-oleic soybean oil, high-oleic safflower oil, high-oleic sunflower oil, mixtures of animal and vegetable fats and oils, beef tallow, castor bean oil, dehydrated castor bean oil, cucumber oil, poppyseed oil, flaxseed oil, lesquerella oil, walnut oil, cottonseed oil, meadowfoam, tuna oil, sesame oils, waste oils/greases, and mixtures thereof.

41. The process of claim 39, wherein the renewable feedstream is selected from palm oil, soybean oil, sunflower oil, canola oil, Jatropha oil, and algae oil.

42. The process of claim 18, wherein the one or more olefins comprise at least one raffinate feedstream.

43. The process of claim 18, wherein the metathesis reaction is a ring opening cross metathesis reaction comprising:
  (i) contacting a cyclic olefin and a second olefinic reactant in the presence of the Group 8 metathesis catalyst under conditions and for a time period sufficient to allow the ring opening cross metathesis reaction to occur; and
  (ii) obtaining a ring opening cross metathesis product.

44. The process of claim 43, wherein the ring opening cross metathesis product is a dimer and is obtained in greater than 50 mol % yield.

45. The process of claim 43, wherein the cross metathesis product is a dimer and is obtained in greater than 70 mol % yield.

46. The process of claim 18, wherein the metathesis reaction is a ring opening metathesis polymerization reaction comprising:
  (i) contacting a cyclic olefin and a second olefinic reactant in the presence of the Group 8 metathesis catalyst under conditions and for a time period sufficient to allow the ring opening metathesis polymerization reaction to occur; and
  (ii) obtaining a ring opening metathesis polymerization product.

* * * * *